(12) United States Patent
Huang et al.

(10) Patent No.: US 11,193,124 B2
(45) Date of Patent: Dec. 7, 2021

(54) SMALL-INTERFERING RNA EXPRESSION SYSTEMS FOR PRODUCTION OF SMALL-INTERFERING RNAS AND THEIR USE

(71) Applicant: City University of Hong Kong, Kowloon (HK)

(72) Inventors: Linfeng Huang, Shatin (HK); Yutian Ren, Kowloon Tong (HK); Hung-chi Cheung, Tuen Mun (HK); Guneet Kaur, Tseung Kwan O (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/351,768

(22) Filed: Nov. 15, 2016

(65) Prior Publication Data
US 2018/0135046 A1 May 17, 2018

(51) Int. Cl.
*C12N 15/113* (2010.01)

(52) U.S. Cl.
CPC ........ *C12N 15/113* (2013.01); *C12N 2310/14* (2013.01); *C12N 2320/12* (2013.01); *C12N 2330/50* (2013.01)

(58) Field of Classification Search
CPC .............. C12N 15/113; C12N 2310/14; C12N 2330/31
See application file for complete search history.

(56) References Cited

U.S. PATENT DOCUMENTS

2007/0117121 A1* 5/2007 Hutchison .......... C12N 15/1096
435/6.12
2015/0337306 A1* 11/2015 Lieberman ............ C12N 15/111
514/44 A

OTHER PUBLICATIONS

Shirane et al., Enzymatic production of RNAi libraries from cDNAs; Nature Genetics, vol. 36, No. 2, pp. 190-196, 2004.*
Synthesize cDNA the SMARTer Way, Clontech Laboratories, Apr. 2009, pp. 10-11. Website: http://catalog.takara-bio.co.jp/PDFSZ200905_10.pdf (Year: 2009).*
Linfeng Huang & Judy Lieberman, Production of highly potent recombinant siRNAs in *Escherichia coli*, Nature Protocols, Dec. 2013, 8(12), 2325-2336 (Year: 2013).*
Linfeng Huang, Jingmin Jin, Padraig Deighan, et al., Efficient and specific gene knockdown by small interfering RNAs produced in bacteria, Nature Biotechnology, Apr. 2013, 31, 350-356 (Year: 2013).*
Linfeng Huang & Judy Lieberman, Production of highly potent recombinant siRNAs in *Escherichia coli*, Nature Protocols, Dec. 2013, 8(12), 2325-2336.
Linfeng Huang, Jingmin Jin, Padraig Deighan, et al., Efficient and specific gene knockdown by small interfering RNAs produced in bacteria, Nature Biotechnology, Apr. 2013, 31, 350-356.

* cited by examiner

*Primary Examiner* — Mindy G Brown
*Assistant Examiner* — Khaleda B Hasan
(74) *Attorney, Agent, or Firm* — Renner Kenner Greive Bobak Taylor & Weber

(57) ABSTRACT

A method of preparing a library of small interfering RNA (siRNA) expression systems for producing siRNA for silencing of target genes by inducing degradation of target gene RNA expression products includes: (i) isolating RNA of one or more target genes from a cell population; (ii) generating RNA fragments from the isolated RNA; (iii) converting the RNA fragments into dsDNA fragments; and (iv) cloning the dsDNA fragments into vectors for forming cloned vectors, each vector including one or more promoters and at least one restriction enzyme site capable of accepting the insertion of at least one dsDNA fragment such that siRNA can be produced. Methods for producing siRNA from the siRNA expression system and methods of identifying a functional target gene for treatment by using the siRNA produced from the siRNA expression system and for identifying RNAi therapeutics are also provided.

8 Claims, 14 Drawing Sheets
(4 of 14 Drawing Sheet(s) Filed in Color)
Specification includes a Sequence Listing.

SMALL-INTERFERING RNA EXPRESSION SYSTEMS FOR PRODUCTION OF SMALL-INTERFERING RNAS AND THEIR USE

SEQUENCE LISTING

The Sequence Listing file entitled "RevSeqListing" having a size of 839 bytes and creation date of 15 Nov. 2016 that was electronically filed with the patent application is incorporated herein by reference in its entirety.

TECHNICAL FIELD

The present invention relates to a method of preparing a library of small interfering RNA (siRNA) expression systems for producing siRNA for silencing of target genes by inducing degradation of target gene RNA expression products from RNA isolated from a cell population especially preferably, but not exclusively, a cell population from a subject, in particular a human, having a disease such as a cancer, an infectious or a genetic disease. Further provided by the present invention is a method for producing siRNA in particular from the siRNA expression system especially preferably, but not exclusively, by using a fermenter. Still further provided are methods of identifying a functional target gene for treatment of a disease in the cell population by using the siRNA produced from the siRNA expression system and for identifying RNAi therapeutics as well as a method for treatment of a subject with the identified RNAi therapeutics. Still further provided is a fermenter and a method for integrated production of a library of siRNA expression systems from RNA isolated from a cell population, for production of siRNA from said library, for determination of the silencing of a target gene in said cell population and for the production of one or more siRNA species identified in said RNAi screen.

BACKGROUND OF THE INVENTION

RNA interference (RNAi) is an evolutionarily conserved biological process existing in many eukaryotic cells. During the RNAi process, short double-stranded (ds) RNA molecules such as siRNAs downregulate gene expression, namely they exert post-transcriptional gene silencing effects typically by inducing the degradation of messenger RNAs (mRNAs) such as by cleavage which is expressed from genes. Typically siRNA interacts with the RNA-induced Silencing Complex (RISC) while the double-stranded siRNA is cleaved and one strand which is referenced as guide strand and corresponds to the antisense strand remains associated with the RISC. The guide strand bound by RISC then links the complex to RNA by base pairing for degradation such as cleavage of the RNA. This leads to a silenced gene. The degradation of mRNA results in no translation from the encoding gene, so no protein can be synthesized from the encoding gene. siRNA has become a highly promising research tool for evaluation of gene functions and for identifying RNAi therapeutics. However, known methods suffer from several drawbacks for example regarding the stability of the siRNA or off-targeting due to non-specific effects of the siRNA such as by interacting with an unintended RNA expression product. Further, the yield of the siRNA produced with usually applied methods from expression systems is limited, which limits the use of commonly used siRNA libraries accordingly.

A novel siRNA design and production system has been described by Huang et al. (Nat Biotechnol, 2013, 31(4):350-6, Huang & Lieberman, Nat Protoc, 2013, 8(12):2325-36). This system utilizes the unique function of a p19 polypeptide, which has the ability to bind to and stabilize dsRNA species produced by endogenous RNase III in *Escherichia coli*, producing a pool of siRNAs within a certain selected gene sequence. Those siRNAs produced in *E. coli* are also called pro-siRNA for prokaryotic siRNA.

There remains a need for siRNA libraries which can be used for high-throughput screening, in particular personalized libraries able to target the whole transcriptome of specific cell lines and subjects allowing for an efficient production of siRNAs obviating the need for sequence selection and which are suitable for identifying functional genes associated with a disease or RNAi therapeutics. In particular, there remains a strong need for methods allowing for the production of large amounts of siRNA in an acceptable period of time from siRNA libraries.

SUMMARY OF THE INVENTION

The present invention provides in a first aspect a method of preparing a library of small interfering RNA (siRNA) expression systems for producing siRNA for silencing of target genes by inducing degradation of target gene RNA expression products such as polypeptide-encoding RNA expression products (mRNA) or non-coding RNA expression products. Said method comprises:

(i) isolating RNA of one or more target genes from a cell population such as from a subject, in particular a human, with a disease such as cancer, in particular the RNA represents the transcriptome of the cell population:

(ii) generating RNA fragments from the isolated RNA;

(iii) converting the RNA fragments into dsDNA fragments in particular comprising Reverse transcription polymerase chain reaction (RT-PCR);

(iv) cloning the dsDNA fragments into vectors for forming cloned vectors, each vector comprising one or more promoters and at least one restriction enzyme site capable of accepting the insertion of at least one dsDNA fragment such that siRNA can be produced.

The vector in particular further comprises a "siRNA-binding polypeptide expression cassette" including a promoter and a sequence encoding a siRNA-binding polypeptide such as a p19 polypeptide and a sequence encoding a siRNA-generating enzyme, in particular a ribonuclease like *Escherichia coli* (*E. coli*) RNase III. The one or more promoters in the vector preferably include at least one T7 promoter. The at least one restriction enzyme site in the vector in particular includes at least one SacI restriction enzyme site.

The siRNA produced in particular has lengths of between about 19 base pairs (bp) to about 23 bp, in particular about 21 bp. The siRNA is preferably at least substantially complementary over its entire length to the target gene RNA expression product or parts thereof, i.e. specific for said target gene.

The method of the present invention of preparing a library of small interfering RNA (siRNA) expression systems in particular further comprises a step (v) of transforming the cloned vectors into bacterial cells which are bacterial cells capable of supporting the siRNA production, in particular *Escherichia coli* (*E. coli*) cells. In particular, one vector is transformed in one bacterial cell, i.e. each population of bacterial cells then represents one or more genes, in particular each population of bacterial cells represents one gene, i.e. is specific for one gene.

Further provided by the present invention is a method for producing siRNA from a siRNA expression system, in particular a siRNA expression system described above, comprising a cloned vector transformed into a bacterial cell, i.e. the siRNA expression system is in form of a bacterial cell, in particular E. coli cell, with a cloned vector. Said method for producing siRNA comprises:

(i) providing said bacterial cells as described above;
(ii) subjecting the bacterial cells to conditions under which siRNA is produced, in particular comprising incubating the bacterial cells;
(iii) optionally isolating the siRNA, in particular including extracting and purifying the siRNA.

In particular, the siRNA is isolated. Alternatively, the bacterial cells are harvested comprising centrifuging for forming pellets and storing them at about −80° C. until siRNA isolation.

Step (ii) is in particular carried out in a fermenter. Such embodiments are particularly suitable for large scale production of siRNA such as of a specific siRNA candidate for further screening.

In another aspect, the present invention refers to a fermenter suitable for use for producing siRNA, in particular a fermenter having an agitation unit comprising means for agitation such as one or more impeller and means for air supply into the mixture, and having an inlet configured for introducing the siRNA expression system and growth medium, means for automatic acid and base supply for adjusting the pH of the mixture comprising the siRNA expression system and growth medium and a bioreactor vessel into which the growth medium and the siRNA expression system can be introduced.

Further provided by the present invention is a method of silencing a target gene in a cell population by inducing degradation of target gene RNA expression products using the siRNA produced as described above comprising providing siRNA as described above from RNA isolated from the cell population and introducing said siRNA into said cell population.

The method of the present invention is in particular advantageous as the siRNA has been produced from siRNA expression systems obtained from RNA of the same cell population into which the siRNA is introduced for silencing of a target gene. The method may comprise a step of determining the silencing efficiency of the target gene, in particular by determining the level of target gene RNA expression products such as by means of qRT-PCR. The target gene can be disease-associated. This means that an overexpression of the target gene is associated with the cause, progression, or maintenance of a disease, e.g. the target gene is an oncogene.

Still further provided is a method of identifying a functional target gene for treatment of a disease by using the siRNA produced as described above comprising:

(i) providing siRNA as described above from a siRNA expression system prepared with the RNA isolated from a cell population, which cell population is from a subject having a disease;
(ii) introducing the siRNA into the cell population;
(iii) analyzing the phenotype of the cell population.

Step (iii) might include comparing the phenotype of the cell population with a negative control, i.e. a cell population of the same cell and tissue type without siRNA or in which non-silencing siRNA has been introduced and/or a positive control of a cell population of the same cell and tissue type in which siRNA has been introduced which is known to influence the phenotype such as siRNA known to silence a specific gene influencing the phenotype of the cell population.

The disease can be, for example, a cancer, an infectious disease or a genetic disease. In particular, the cell population comprises cancer cells and step (iii) includes determining the cell viability of the target cell population such as with commercially available assays like the HCS VIABILITY ASSAY™, the CELLTITER-GLO™ (CTG) Luminescent Cell Viability Assay or flow cytometry and comparing the cell viability with a negative control, wherein a cell growth decreased to less than 60% compared to a negative control indicates silencing of a gene that is essential for the growth of the cancer cells.

In another aspect, the present invention refers to a method of identifying RNAi therapeutics by using the siRNA produced as described above comprising:

(i) providing siRNA as described above from a siRNA expression system prepared with the RNA isolated from a cell population, in which the cell population harbors an increased expression or activity of a gene indicative of a certain disease;
(ii) introducing the siRNA into the cell population;
(iii) determining the silencing efficiency comprising determining the level of RNA expression products from said gene in particular by means of qRT-PCR.

In particular, an at least 80% decrease in the levels of RNA expression products compared to a negative control indicates that the siRNA is a potential RNAi therapeutic.

Still further provided by the present invention is a method for the integrated production of a library of siRNA expression systems for producing siRNA prepared from RNA isolated from a cell population, production of siRNA from said library, determination of silencing a target gene in said cell population such as by determining the phenotype or level of RNA expression products from the target gene compared to a negative control and/or a positive control and production of one or more siRNA species leading to a predetermined phenotype and/or predetermined silencing efficiency in particular by using the fermenter of the present invention. Hence, the present invention further relates to a method for producing siRNA leading to a predetermined phenotype and/or predetermined silencing efficiency for a target gene comprising steps of:

A) preparing a library of small interfering RNA (siRNA) expression systems for producing siRNA comprising isolating RNA from a cell population from a subject with a disease such as cancer; generating RNA fragments from the isolated RNA; converting the RNA fragments into dsDNA fragments; cloning the dsDNA fragments into vectors for forming cloned vectors, each vector comprising one or more promoters and at least one restriction enzyme site capable of accepting the insertion of at least one dsDNA fragment such that siRNA can be produced, and transforming the vectors into bacterial cells;

B) producing siRNA from the siRNA expression system of step A) comprising subjecting the bacterial cells to conditions under which siRNA is produced and isolating the siRNA; in particular step B) comprises introducing the bacterial cells into micro-well plates in particular such that one well receives one population of bacterial cells; subjecting the micro-well plates to conditions under which the bacterial cells grow, and inducing siRNA production; wherein isolating the siRNA in particular comprises initiating lysis of the bacterial cells such as by mechanical forces;

centrifuging the lysate for obtaining a supernatant comprising the siRNA and a residue; extracting and purifying the siRNA in the supernatant comprising contacting the supernatant with magnetic beads for affinity purification and elution of siRNAs, subjecting the eluate to anion exchange chromatography with strong anion exchange magnetic beads and/or solid phase reversible immobilization beads;

C) silencing a target gene in the cell population comprising introducing the siRNA into the cell population, analyzing the phenotype of the cell population and/or determining the silencing efficiency comprising determining the level of RNA expression products from said target gene; in particular step C) comprises introducing the cell population into multi-well plates such that each well of the multi-well plate receives siRNA produced from a different population of bacterial cells, in particular each well receives siRNA specific for one gene and analyzing the phenotype of the cell population such as the cell viability for example by means of HCS or CTG and/or determining the silencing efficiency comprising determining the level of RNA expression products from said gene; step C) may further comprise sequencing the siRNA or dsDNA fragment in the cloned vector to identify the target gene;

D) selecting the siRNA leading to a predetermined phenotype and/or having a predetermined silencing efficiency and producing siRNA from bacterial cells according to step A) which are able to produce said siRNA comprising subjecting the bacterial cells to conditions under which the siRNA is produced and isolating the siRNA for further screening, wherein step D) in particular includes introducing a mixture comprising the bacterial cells and growth medium in a fermenter having an agitation unit comprising means for agitation and means for air supply into the mixture and having an inlet configured for introducing the siRNA expression system and means for automatic acid and base supply for adjusting the pH of the mixture; agitating the mixture at a temperature between about 15° C. and about 40° C. such as between about 30° C. and about 40° C. and a pH of between about 6.5 and about 7.5; inducing the production of the siRNA; and maintaining the bacterial cells in the mixture for at least about 1 h under conditions under which the bacterial cells grow; and wherein isolating the siRNA in particular comprises initiating lysis of the bacterial cells such as by mechanical forces; centrifuging the lysate for obtaining a supernatant comprising the siRNA and a residue; extracting and purifying the siRNA in the supernatant comprising contacting the supernatant with magnetic beads for affinity purification and elution of siRNAs, subjecting the eluate to anion exchange chromatography with strong anion exchange magnetic beads followed by contacting the eluate with solid phase reversible immobilization beads.

The library of siRNA expression systems of the present invention represents a "personalized" functional diagnostic tool particularly suitable for the identification of disease-causing genes of the exact isoform and as expressed in the cell population and of RNAi therapeutics. So a respective RNAi screen could be much more efficient than the one obtained with conventional methods. The present method is cost-effective and easily adaptable to an industrial setting for producing various libraries of personalized, i.e. cell line and subject specific siRNA expressing systems. The library of siRNA expression systems can cover all expressed genes, i.e. the transcriptome of any cell population of any species with minimal off-targeting effects and minimized false positive and false negative rates of obtainable siRNAs. Even a pool of siRNAs is producible which allows detecting and analyzing synergistic effects of genes contributing to certain phenotype.

The resulting library of siRNA expression systems can be used similarly as conventional siRNA libraries. The library of siRNA expression systems is particularly suitable for genome-wide loss-of-function analysis, i.e. RNAi screen to identify essential functional genes for a particular biological pathway or a disease process.

Furthermore, an identified candidate siRNA can be produced in large quantities using the fermenter of the present invention which means an at least 10-fold increase compared to commonly used methods for producing siRNAs. Said method can be adapted to an industrial setting to produce large amounts of siRNAs. The siRNAs can be further provided with high purity. The siRNAs can then be used in various downstream applications including, for example, validation of candidate genes, gene functional studies in cell lines and in animal models and as RNAi therapeutics.

In order to prove the several advantages of the methods of the present invention, the inventors have prepared a library of siRNA expression systems in HeLa cancer cells, produced siRNA from said library and used them for identifying functional genes involved in cancer cell proliferation in HeLa cancer cells. The candidate genes include the D-3-phosphoglycerate dehydrogenase (PHGDH) gene, which was previously identified by a conventional RNAi screen. These results confirm the high efficiency of the methods of the present invention. Thus, the methods of the present invention represent highly promising and advantageous options for producing commercial products for RNAi screens in particular libraries of siRNA expression systems specific for various cell types and disease models such as human cancers, genetic diseases and viral infections.

Furthermore, the methods of the present invention allow for producing personalized RNAi therapeutics guided by patient's own disease cells such as primary cancer cells isolated from a cancer patient. This allows for specifically identifying essential functional genes for the patient's specific type of cancer. For cancer treatment, those genes could be targeted by the present gene-specific drugs, namely the produced siRNAs or alternatively other types of gene-specific drugs. The siRNAs against those target genes can be quickly produced in large quantities and then be made into RNAi therapeutics for treating the cancer by the methods of the present invention.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A, B, and C thus refer to the cloning efficiency and siRNA silencing efficiency.

FIGS. 5A, B, and C thus refer to an embodiment of the method for producing siRNA with siRNA isolation including extraction and purification in multi-well plates.

FIGS. 6A, B, and C thus refer to a siRNA screen, namely the identification of functional target genes essential for cancer cell survival.

FIGS. 7A and B thus refer to a comparison between siRNA screen data using high content screen (HCS) and CELLTITER-GLO™ (CTG) assays.

FIGS. 8A and B thus refer to a fermenter of the present invention which is particularly suitable for large scale production of siRNAs.

DETAILED DESCRIPTION OF THE INVENTION

Figure 1:
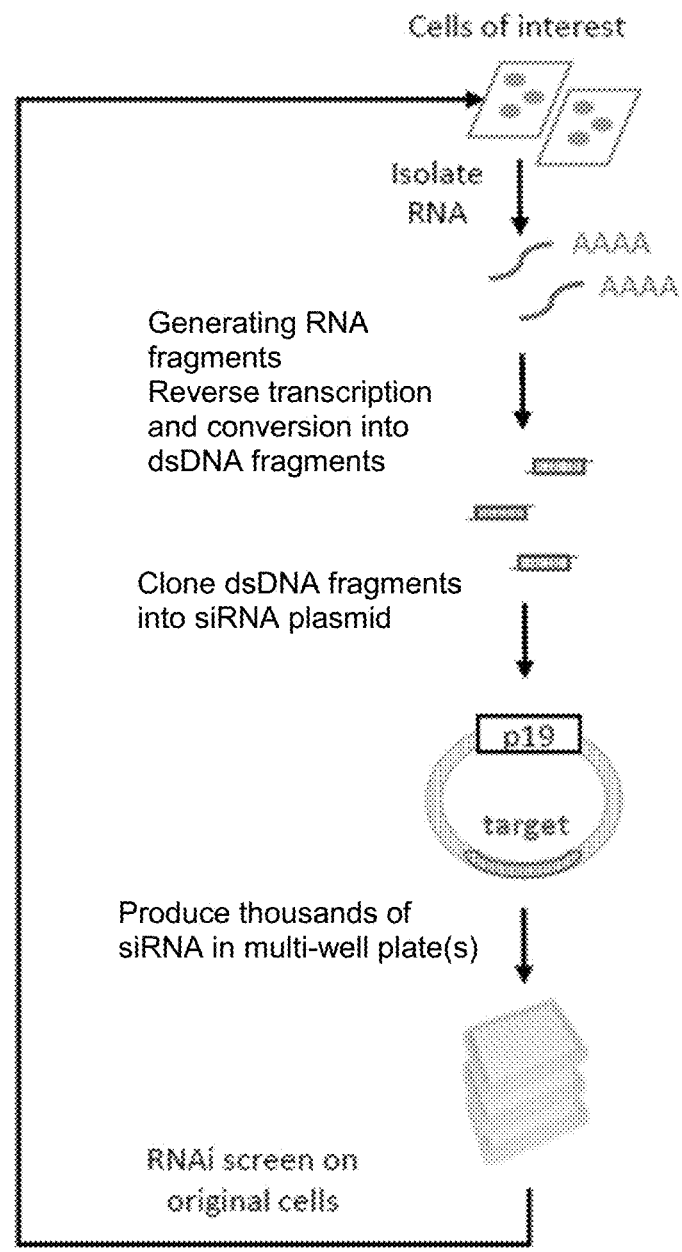
FIG. 1 is a schematic representation of an embodiment of the method of the present invention for producing a library of siRNA expression systems and the use for RNAi screens of the cell population from which the RNA has been isolated such as for silencing of target genes, for identifying a functional target gene for treatment and/or for identifying RNAi therapeutics.

Unless otherwise defined, all technical terms used herein have the same meaning as commonly understood by one of skill in the art to which the invention belongs. Unless otherwise specified herein standard procedures can be used in the methods of the present invention as described, for example, in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise. Other than in the working examples, or where otherwise indicated, all numbers used herein should be understood as modified in all instances by the term "about." The term "about" when used in connection with number can mean, for example, ±2%.

The present invention provides a method of preparing a library of small interfering RNA (siRNA) expression systems for producing siRNA for silencing of target genes by inducing degradation of target gene RNA expression products, said method comprises:

(i) isolating RNA of one or more target genes from a cell population;

(ii) generating RNA fragments from the isolated RNA;

(iii) converting the RNA fragments into dsDNA fragments;

(iv) cloning the dsDNA fragments into vectors for forming cloned vectors, each vector comprising one or more promoters and at least one restriction enzyme site capable of accepting the insertion of at least one dsDNA fragment such that siRNA can be produced, in particular such that siRNA precursors can be expressed.

The expression "library of siRNA expression systems" includes siRNA expression systems in form of cloned vectors such as cloned plasmids or in form of bacterial cells into which the cloned vectors have been transformed which can be used for producing siRNA for silencing of target genes, in particular the library of siRNA expression systems includes bacterial cells into which the cloned vectors have been transformed. Said library includes a plurality of populations of siRNA expression systems each population specific for one or more genes or gene fragments, in particular each population specific for one gene. A "population" means siRNA expression systems of the same type, namely with the same cloned vector expressing the same siRNAs. Most preferably, each population of siRNA expression systems can produce multiple siRNAs specific for one gene or gene fragment different from the gene or gene fragment of other populations.

A "siRNA expression system" likewise includes cloned vectors or bacterial cells into which the cloned vectors have been transformed which can be used for producing siRNAs, in particular which are able to express siRNA precursors which can be processed into siRNA, which siRNA precursors are dsRNA with about 100 or more base pairs in length including hairpin dsRNA. Said siRNA precursors can be subsequently processed, in particular cleaved, to siRNA in particular by a siRNA-generating enzyme present in the bacterial cell such as a siRNA-generating enzyme encoded in the cloned vector like a RNase III as disclosed in US 2015/0337306A1 incorporated herein by reference, in particular an *E. coli* RNase III (e.g. NCBI Gene ID: 947033) or an RNase III from any other bacterial species. A siRNA-generating enzyme is an enzyme, namely a polypeptide, with RNase activity which can cleave the (long) dsRNA in such a way that siRNAs can be formed.

The populations of siRNA expression systems in particular differ with respect to the silenced genes. Namely, each population of expression systems can be used to produce siRNAs which is preferably at least substantially complementary over its entire length to at least a part of RNA expression products from one or more genes able to silence that genes, in particular at least substantially complementary over its entire length to RNA expression products from one gene and able to silence that gene. The library can be, for example, in form of multi-well plates having a population of expression systems in each well provided growth medium. Each well of a multi-well plate in particular comprises a different population of siRNA expression systems, in particular in form of bacterial cells with a cloned vector. Said library can comprise at least 100, preferably at least 500 and in particular more than 900 different populations of siRNA expression systems. In particular, the library of siRNA expression systems comprises populations of expression systems each able to produce siRNAs at least substantially complementary over its entire length to RNA expression products from different target genes, i.e. each population is specific for a target gene.

Small interfering RNAs are small double-stranded RNAs (dsRNAs) also known as silencing RNA. siRNA operates within the RNA interference (RNAi) pathway, where they interfere with the expression of genes by degrading RNA expression products of the gene with at least partially complementary sequence of at least a part of the siRNA to at least a part of the sequence of the RNA expression products of the gene resulting in no translation to the polypeptide expression product of said gene in case the RNA expression product encodes a polypeptide, i.e. it is mRNA, or an otherwise inhibition of the target gene expression in case the RNA expression product is non-coding.

As used herein, the expressions "silencing of genes", "silencing", or "RNAi" refer to a phenomenon where an agent for causing RNAi, in the present invention siRNA, causes the specific degradation of RNA expression products, thus suppressing the expression of polypeptide expression products in case the RNA expression product is an mRNA expression product or otherwise suppressing gene expression from said target gene in case the RNA expression product is non-coding. Silencing of a gene in particular means a decrease in the level of a RNA expression product from the gene in a cell which is statistically significant, further preferred the level of RNA expression products of a gene in a cell is decreased by at least about 20%, still further preferred by at least about 50%, more preferably at least by about 60% such as by at least 80% or more compared to the level in a cell without the presence of the siRNA or with non-silencing siRNA. As used herein, the term "statistically significant" means a result that generally is at least two standard deviations above or below the mean of at least three separate determinations of a control and/or that is statistically significant as determined by Student's t-test or other art-accepted measures of statistical significance.

The term "gene" use herein means a nucleic acid sequence, namely a DNA sequence able to express mRNA and usually a polypeptide as its expression products, in particular which can be transcribed to mRNA and further translated to a polypeptide. The term "target genes" includes all genes which can be silenced by the siRNA namely which RNA expression products can be degraded such as cleaved by the siRNA.

The term "expression" refers to the processes involved in producing RNA and polypeptides from DNA including transcription, transcript processing, translation and protein folding, modification and processing. "Expression products" include RNA transcribed from a gene, and polypeptides obtained by translation of mRNA transcribed from the gene as well as non-coding RNA.

"Polypeptides" which is used interchangeably with the term "protein" means a polymer of two or more amino acids connected to each other by peptide bonds between amino groups and carboxy groups of adjacent amino acid residues. The amino acid residues can be modified (e.g., phosphorylated, glycated, glycosylated, etc.).

DNA and RNA sequences means nucleic acid sequences, i.e. sequences from units of deoxyribonucleic acid and ribonucleic acid, respectively. Isolated RNA from a cell population is usually single-stranded. dsDNA or dsRNA used herein means double-stranded DNA and RNA, respectively. Double-stranded DNA or RNA comprises two strands of DNA and RNA, respectively, commonly referred to as sense strand and antisense strand which are in particular at least substantially complementary. This does not exclude the presence of loop structures. Namely, dsRNA includes those RNAs comprising a single-strand RNA that doubles back on itself to form a double-stranded structure having a loop part, e.g. a hairpin RNA.

The term "complementary" refers to the base pairs A:T, G:C and A:U formed between two strands, I.e. formed between sense and antisense strand. "Substantially complementary" as used herein in particular refers to a nucleotide sequence having at least about 80% complementarity over the entire length of said sequence with another nucleotide sequence or part thereof, e.g. at least about 90% complementary, at least about 95% complementary, at least about 98% complementary, at least about 99% complementary, or 100% complementary. I.e. nucleotide sequences are substantially complementary even if less than 100% of the bases are complementary, e.g. the sequences can be mismatched at certain bases. "Partially complementary" means less than significantly complementary, i.e. a part of a sequence is complementary to a part of another sequence. For siRNA, the expression "complementary to RNA" or "at least substantially complementary to RNA" always refers to one strand of the siRNA, namely the guide strand of the siRNA which interacts with the RNA expression product.

RNA isolated from the target gene in step (i) includes mRNA, also referenced as polypeptide-encoding RNA, as well as non-coding RNA, which does not encode a polypeptide but otherwise modulates target gene expression. mRNA is known as messenger RNA, namely RNA specifying the amino acid sequence of the polypeptide expression product of a gene. Accordingly, "RNA expression product" of a target gene is the mRNA which is an expression product from said gene or non-coding RNA which can otherwise modulate the target gene expression. Said mRNA or non-coding RNA comprises a nucleotide sequence with which one strand of the siRNA (the guide strand) can interact thereby causing RNAi. The term "total RNA" in particular includes mRNA, non-coding RNA including ribosomal RNA (rRNA). The RNA used in step (i) preferably represents the transcriptome of the cell population, namely the RNA molecules transcribed from the cell population specific genome, in particular mRNA of all transcribed genes.

The cell population can be from any subject. The subject can be a human or animal, in particular a mammal such as a human. The cell population can have certain phenotype. In particular, the cell population is from a subject with certain disease such as cancer. In particular embodiments of the present invention, the cell population comprises and further preferred is formed by cancer cells such as from a human.

The siRNA which can be produced preferably has lengths of between about 19 base pairs (bp) to about 23 bp, in particular about 19 bp to about 22 bp, preferably the siRNA is about 21 bp long. The siRNA is preferably at least substantially complementary over its entire length to RNA expression products, which either encode a polypeptide or are non-coding, from a target gene, wherein one siRNA is in particular at least substantially complementary over its entire length to the RNA expression product from one target gene. In some embodiments, the siRNA can be blunt-ended. In alternative embodiments, the siRNA can comprise a 3' and/or 5' overhang on each strand having a length of about 0, 1, 2, 3, 4, or 5 nucleotides. The length of the overhang is independent between the two strands. The siRNA molecules can also comprise a 3' hydroxyl group and a 5' phosphate group.

Step (i) of the method in particular comprises extracting total RNA from the cell population and removing rRNA. It may include extraction of total RNA with organic solvents or by solid-phase extraction on silica as known to one of skill in the art. The removal of rRNA can be, for example, carried out via selection of mRNA via hybridization by the tail or removal of rRNA via hybridization such as with commercially available kits. The isolated RNA of the one or more target genes from the cell population in particular comprises and is more preferably mRNA.

Step (ii) can comprise methods known to one of skill in the art for fragmentation of RNA like enzymatic, metal ion, heat, and/or sonication.

The RNA fragments generated in step (ii) can have a length of several hundred nucleotides as suitable for cloning into a vector preferably they have a length of about 100 nucleotides to about 700 nucleotides, in particular at least about 200 nucleotides to about 700 nucleotides.

Step (iii) in particular comprises Reverse transcription polymerase chain reaction (RT-PCR).

It preferably includes a reverse transcription translating the RNA fragments from step (ii) to a first strand cDNA. During this process, a mixture of random hexa-nucleotides is in particular used as random primers to prime DNA synthesis along multiple sites of the template RNA. A recombinant M-MuLV reverse transcriptase also referenced as PROTOSCRIPT™ II Reverse Transcriptase is preferably used as key enzyme to generate the first strand cDNA which can then be directly used for a second strand synthesis. Step (iii) then further includes a second strand synthesis step for generating double-stranded cDNA from the first strand cDNA. During this process, a second strand synthesis enzyme mix is preferably optimized to convert short first strand cDNA to double-stranded cDNA with the random primers as preferably existing in the previous reverse transcription system. The dsDNA fragments generated herein can be subsequently converted to blunt-end dsDNA fragments for further steps.

The term "vector" used herein refers to nucleic acid constructs designed for delivery to a host cell, in particular a bacterial cell. A vector can be viral or non-viral. Preferably the vector is a plasmid. Plasmids are double-stranded and generally circular DNA sequences. The vector is an expression vector, i.e. a vector that has the ability to incorporate and express nucleic acid fragments in a host cell in particular a bacterial cell.

Plasmids can include, but are not limited to the plasmid vectors disclosed in US 2015/0337306A1 which are incorporated herein by reference, and include pBR322, pBR325, pACYC177, pACYC184, pUC8, pUC9, pUC18, pUC19, pLG339, pR290, pKC37, pKCIOI, SV 40, pBluescript II SK+/− or KS+/−, pQE, pIH821, pGEX, pET series. The plasmid can, for example be a pGEX plasmid.

The term "cloned vector" or "cloned plasmid" is used herein for the vector (such as plasmid) obtained after cloning the dsDNA fragments into the vector (such as plasmid).

In particular, one or more dsDNA fragments are cloned into one vector. In embodiments of the present invention, one dsDNA fragment is cloned into one vector in step (iv), i.e. one vector is specific for one gene (or gene fragment) and siRNAs can be produced from said vector targeting said one gene. This allows for preparing a library of siRNA expression systems having populations of siRNA expression systems with each population being able to produce siRNAs preferably at least substantially complementary over its entire lengths to RNA expression products of one gene different from the gene of the other populations. In alternative embodiments, two or more dsDNA fragments are cloned into one vector, i.e. multiple gene fragments are ligated into one vector able to produce siRNAs preferably at least substantially complementary over its entire lengths to RNA expression products of two or more genes.

In particular, cloning the dsDNA fragments into the vectors in step (iv) includes ligating a sense sequence, an antisense sequence and optionally a sequence that forms a loop, in particular between two opposing promoters into a vector, also referenced as "siRNA producing cassette", in particular as a siRNA precursor expression cassette in the cloned vector.

Preferably, the vector further comprises a "siRNA-binding polypeptide expression cassette" including a promoter and a sequence encoding a siRNA-binding polypeptide in particular a p19 polypeptide and optionally a siRNA-generating enzyme, in particular a ribonuclease like an *Escherichia coli* (*E. coli*) RNase III. One of skill in the art will understand that the method of the present invention could also use sequences encoding a siRNA-generating enzyme such as a RNase III from any other bacterial species. In preferred embodiments of the present invention, the vector is a plasmid further comprising a siRNA-binding polypeptide expression cassette including a promoter, a sequence encoding a siRNA-binding polypeptide and a sequence encoding a siRNA-generating enzyme, wherein the siRNA-binding polypeptide is a p19 polypeptide and the siRNA-generating enzyme is an *E. coli* RNase III.

siRNA-binding polypeptides such as p19 polypeptides in particular but not limited to the p19 polypeptide such as tombusvirus p19 (NCBI Gene ID: 1493957) are able to bind to the siRNA and in particular include those as disclosed in US 2015/0337306A1 which are incorporated herein by reference. The siRNA-binding polypeptide is in particular a p19 polypeptide as disclosed in US 2015/0337306A1, i.e. selected from a p19 polypeptide such as tombusvirus p19 polypeptide. Further preferred, the siRNA-binding polypeptide has a purification tag suitable for purification of the siRNA-binding polypeptide and siRNAs bound to the siRNA-binding polypeptide. The purification tag can bind to another moiety such as on a matrix or a resin with affinity for the purification tag such as Ni-NTA resin. Particular purification tags include histidine tags ("His-tagged") such as disclosed in US 2015/0337306A1 which are incorporated herein by reference. The siRNA-binding polypeptide is in particular a His-tagged p19 polypeptide.

The vector is in particular able to express a siRNA-binding polypeptide, in particular a p19 polypeptide such as His-tagged p19 polypeptide, and a siRNA-generating enzyme like a RNase III or siRNA-binding polypeptide, in particular p19 such as His-tagged p19, fused to a siRNA-generating enzyme like an *E. coli* RNase III. Such expression of siRNA-generating enzyme like an *E. coli* RNase III will enhance the siRNA production.

The one or more promoters in the vector preferably include a T7 promoter, i.e. a T7 promoter sequence which is known to one of skill in the art. In particular, the vector comprises two or more promoters, in particular two or more T7 promoters. The "siRNA producing cassette" in the cloned vector preferably comprises two opposing promoters, more preferably T7 promoters, with the at least one dsDNA fragment in between.

The vector may further comprise a promoter control operator such as a lac operator such as as part of a lac operon arranged to control the production of the siRNA such as the expression of siRNA precursors depending on the presence or absence of an inducer. In such embodiments of the present invention, expression of the siRNA precursor can be initiated and/or enhanced by adding the inducer. Suitable inducers are those as described in US 2015/0337306A1 incorporated herein by reference. A preferred inducer is Isopropyl β-D-1-thiogalactopyranoside (IPTG). The sequence of a lac operator and lac operon is known to one of skill in the art. In preferred embodiments of the present invention, the one or more promoters are T7 promoters and the vector further comprises a lac operator such as as part of a lac operon.

Figure 2A:
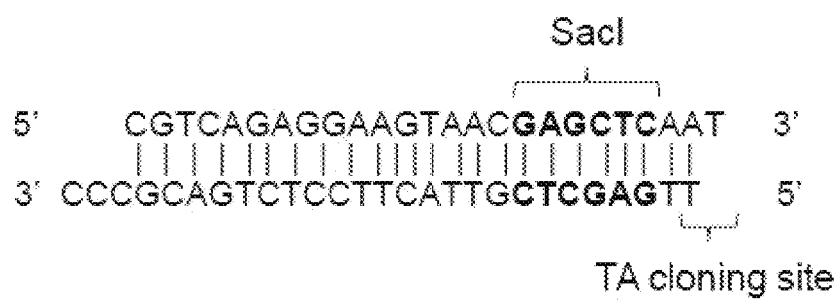
FIG. 2A shows a preferred adaptor (SEQ. ID. NO: 1, and SEQ. ID. NO: 2) having a SacI restriction enzyme site and a TA cloning site for ligation with the dsDNA fragments.
Figure 2B:
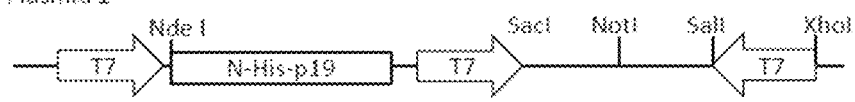
FIG. 2B is a schematic representation of preferred plasmid designs particularly suitable for producing siRNA expression system libraries. Plasmid 1 expresses His-tagged p19 polypeptide. Plasmid 2 expresses a His-tagged p19 polypeptide fused with E. coli RNase III. Plasmid 3 expresses a His-tagged p19 polypeptide and E. coli RNase III. "T7" is the T7 promoter. SacI represents the SacI restriction enzyme site.
Figure 2B:
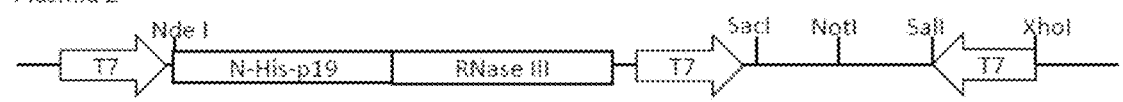
Figure 2B:
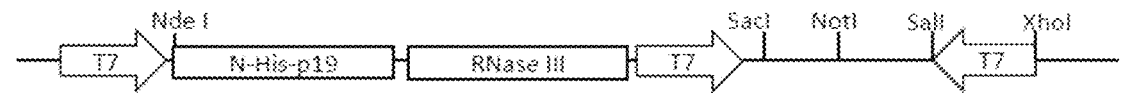

The vector thus in particular contains at least one siRNA-binding polypeptide such as a p19 polypeptide expression cassette and a siRNA producing cassette (FIG. 2B, Plasmid 1). The siRNA producing cassette is formed by two opposing promoters (e.g. T7 promoter, see FIG. 1) flanking the inserted dsDNA fragments. Additionally, the vector can have the ability of siRNA-generating enzyme such as an *E. coli* RNase III overexpression either by siRNA-generating enzyme such as an *E. coli* RNase III fusion to a siRNA-binding polypeptide such as a p19 polypeptide (FIG. 2B, Plasmid 2) or by expressing a separate siRNA-generating enzyme such as an *E. coli* RNase III on the same transcript (FIG. 2B, Plasmid 3). An overexpression of a siRNA-generating enzyme such as an *E. coli* RNase III can further enhance siRNA production. "Overexpression" of a siRNA-generating enzyme, for example, means an expression of said siRNA-generating enzyme exceeding the expression in wild-type *E. coli* by at least about 30%.

The at least one restriction enzyme site in the vector in particular includes at least one SacI restriction enzyme site.

Step (iv) may in particular comprise:

a) ligating the DNA fragments with an adaptor comprising at least one restriction enzyme site matching the at least one restriction enzyme site in the vector;

b) amplifying the dsDNA fragments with a primer matching the adaptor in particular carried out by means of PCR;

c) digesting the dsDNA fragments by a restriction enzyme able to recognize the restriction enzyme site on the adaptor, in particular by a SacI restriction enzyme;

d) ligating the digested dsDNA into the vector.

The restriction enzyme site of the adaptor is in particular a SacI restriction enzyme site and the adaptor comprises SEQ. ID. NO:1 and SEQ. ID. NO:2 as complementary strand, in particular is formed by SEQ. ID. NO:1 and SEQ. ID. NO:2 as complementary strand such as shown in FIG. 2A. The restriction enzyme able to recognize the restriction enzyme site on the adaptor is in particular a SacI restriction enzyme.

In preferred embodiments of the present invention, step a) includes adding the adaptor and a ligase, in particular it includes adding a ligase and an adaptor having a SacI restriction enzyme site based on TA cloning, i.e. based on the ability of adenine and thymidine of different DNA fragments to hybridize and in the presence of a ligase become ligated together.

The method of the present invention of preparing a library of small interfering RNA (siRNA) expression systems preferably further comprises a step (v) of transforming the cloned vectors into bacterial cells which are cells capable of supporting the siRNA production.

Suitable bacterial cells are those as disclosed in US 2015/0337306A1 incorporated herein by reference. Non-limiting examples of bacterial cells suitable for use in the present invention include *Escherichia coli* cells including *E. coli* BL21, *E. coli* Tuner, *E. coli* Rosetta, *E. coli* JM101, and derivatives of any of the foregoing. Bacterial cells for protein expression are commercially available, e.g. EXPRESS™ Competent *E. coli* (Cat. No. C2523; New England Biosciences; Ipswich, Mass.). One of skill in the art will understand that the method of the present invention could also utilize bacterial species other than *E. coli*.

Preferably, the bacterial cells are selected from *E. coli* cells such as with an expression of siRNA-generating enzyme such as *E. coli* RNase III and an expression of a siRNA-binding polypeptide, in particular a p19 polypeptide, in particular with an expression of the siRNA-generating enzyme significantly exceeding the expression in wild-type *E. coli* cells which preferably means an expression of siRNA-generating enzyme such as *E. coli* RNase III which is at least 20%, further preferred at least 30% increased compared to wild-type *E. coli* cells, i.e. in particular has an overexpression of a siRNA-generating enzyme such as an *E. coli* RNase III. In particular embodiments of the present invention, the bacterial cells are selected from *E. coli* cells and the vectors transformed into the bacterial cells comprise a siRNA-binding polypeptide expression cassette including a promoter, a sequence encoding a siRNA-binding polypeptide and a sequence encoding a siRNA-generating enzyme, wherein the siRNA-binding polypeptide is preferably a His-tagged p19 polypeptide and the siRNA-generating enzyme is preferably an *E. coli* RNase III.

In particular, one vector is transformed in one bacterial cell, i.e. each population of said bacterial cells then represents one or more genes, in particular represents one gene, i.e. each population of bacterial cells can be used for preparing siRNAs preferably at least substantially complementary over its entire lengths to RNA expression products from one or more genes, i.e. target gene(s) different from the targeted gene(s) of other bacterial cell populations, in particular to RNA expression products from one target gene different from the target gene of other populations of bacterial cells.

FIG. 1 shows an embodiment of the method of the present invention for producing a library of siRNA expression systems which can be used for siRNA production and RNAi screens of the cell population from which the RNA has been isolated such as for silencing of target genes, for identifying a functional target gene for treatment and/or for identifying RNAi therapeutics, wherein RNA is isolated from a cell population ("cells of interest"), RNA fragments are generated and the fragments are converted into dsDNA fragments which are cloned into a vector which comprises a siRNA-binding polypeptide in form of a p19 polypeptide ("p19").

Further provided by the present invention is a method for producing siRNA from a siRNA expression system in form of bacterial cells, i.e. in particular bacterial cells comprising a cloned vector transformed into the bacterial cells. The siRNA expression system is in particular a siRNA expression system as described above, i.e. are provided as described above. The bacterial cell can be from any species although *E. coli* cells are preferred.

In particular, the bacterial cells are selected from *E. coli* cells and the vector comprises a siRNA-binding polypeptide expression cassette including a promoter, a sequence encoding a siRNA-binding polypeptide and a sequence encoding a siRNA-generating enzyme, wherein the siRNA-binding polypeptide is a His-tagged p19 polypeptide and the siRNA-generating enzyme is *E. coli* RNase III.

Said method for producing siRNA comprises:

(i) providing a siRNA expression system in form of bacterial cells, in particular a siRNA expression system in form of bacterial cells prepared as described above, i.e. prepared comprising steps as described above of isolating RNA of one or more target genes from a cell population; generating RNA fragments from the isolated RNA; converting the RNA fragments into dsDNA fragments; and cloning the dsDNA fragments into vectors for forming cloned vectors, each vector comprising one or more promoters and at least one restriction enzyme site capable of accepting the insertion of at least one dsDNA fragment such that siRNA can be produced, in particular allowing the expression of siRNA precursors;

(ii) subjecting the bacterial cells to conditions under which siRNA is produced, in particular comprising incubating the bacterial cells;

(iii) optionally isolating the siRNA, in particular including extracting and purifying the siRNA.

The term "isolated" as used herein means separating the siRNA from other components such as from the bacterial cells and other DNA or RNA sequences or polypeptides that are present resulting from the materials used and conditions applied for producing the siRNA. In particular, isolating the siRNA comprises extracting and purifying the siRNA.

"Conditions under which siRNA is produced" means applying conditions such as the addition of an initiator or certain temperature or pH suitable to initiate and/or enhance the production of the siRNA, in particular the expression of siRNA precursors and their processing to siRNAs.

In preferred embodiments of the present invention, the siRNA is isolated. In alternative embodiments of the present invention, the bacterial cells are harvested comprising centrifuging for forming pellets and storing them at about −80° C. until siRNA isolation.

In particular embodiments of the present invention, step (ii) is carried out in multi-well plates, for example, 96-well plates or more, such that a single population of siRNA expression systems, i.e. a single population of bacterial cells, is received in each well, i.e. such that each well represents a specific target gene. Such embodiment allows for an advantageous high-throughput production of siRNA and subsequent RNAi screen. Step (ii) can comprise steps of:

introducing the bacterial cells into micro-well plates in particular such that one well receives one population of bacterial cells;

optionally sealing the micro-well plate with a film, in particular a breathable film;

subjecting the micro-well plates to conditions under which the bacterial cells grow such as by shaking for up to about 21 h, in particular by placing the optionally sealed micro-well plates in an incubator shaker such as at about 15° C. to about 40° C. such as at about 30° C. to about 40° C., in particular at about 37° C.;

inducing the production of siRNA, preferably by adding an inducer, in particular IPTG when the bacterial cells are in the exponential growth phase.

Figure 4:
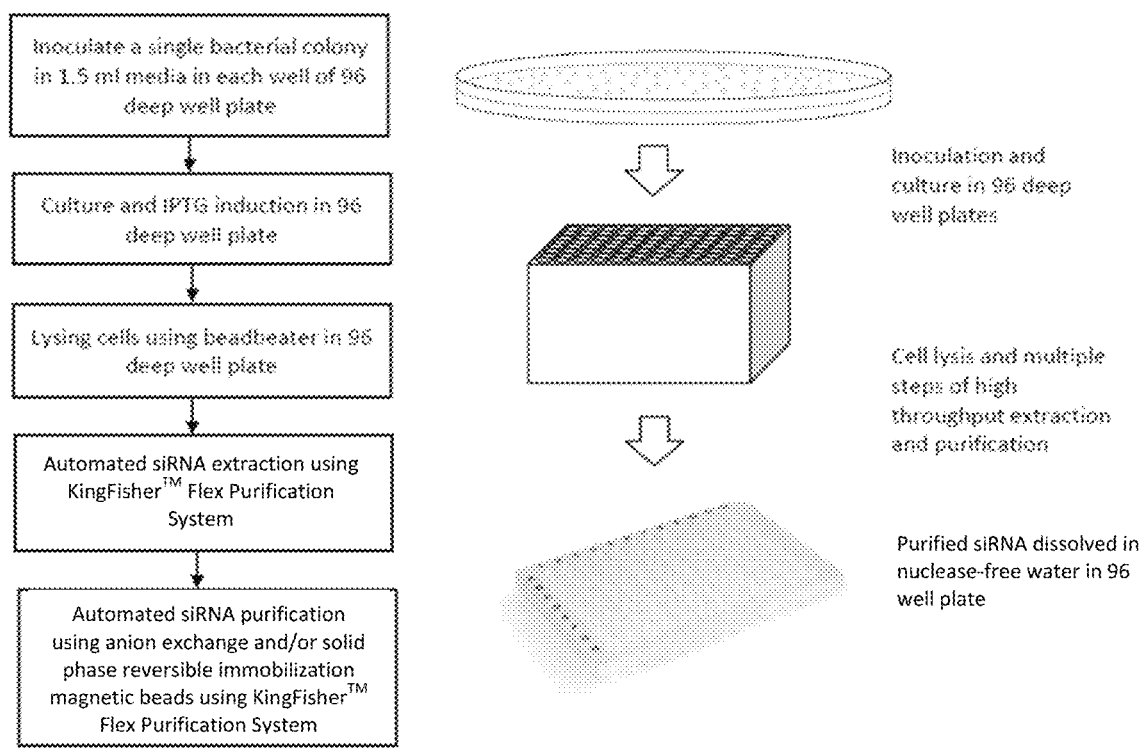
FIG. 4 is a schematic representation of an embodiment of the present invention of high-throughput siRNA production and isolation.

FIG. 4 shows an embodiment of the method of the present invention for high-throughput siRNA production and isolation comprising introducing the bacterial cells into micro-well plates (here 96 well plate(s)) by inoculating a single bacterial population ("single bacterial colony") in each well, the bacterial cells are subjected to conditions under which the bacterial cells grow ("culture") and the siRNA production is induced by means of IPTG. The siRNA is then isolated comprising lysing the cells in a beadbeater followed by an automated siRNA extraction using KINGFISHER™ Flex Purification System (Thermo Fisher Scientific) and purification using anion exchange and/or solid phase reversible immobilization magnetic beads using KINGFISHER™ Flex Purification System.

In preferred embodiments, step (ii) is carried out in a fermenter. Such embodiments are in particular suitable for large scale production of siRNA such as of a specific siRNA candidate, i.e. siRNA population for further screening.

Step (ii) in preferred embodiments comprises:

a) introducing a mixture comprising the bacterial cells and growth medium in a fermenter (1) having an agitation unit (2) comprising means for agitation such as one or more impeller (3) and means for air supply into the mixture (4, 5) and having an inlet configured for introducing the mixture (6) and means for automatic acid and base supply for adjusting the pH of the mixture (7, 8);

b) agitating the mixture at a temperature between about 15° C. and about 40° C. such as between about 30° C. and about 40° C. and a pH of between about 6.5 and about 7.5;

c) inducing the production of siRNA;

d) maintaining the bacterial cells in the mixture for at least 1 h under conditions under which the bacterial cells grow.

The fermenter in particular comprises a bioreactor vessel (19) into which the growth medium (20) and the bacterial cells (21) are introduced.

The agitation unit (2) in particular comprises means for agitation such as one or more impeller (3) and means for air supply into the mixture (4, 5) comprising a tube (5), a filter (18) and a microsparger (4), in particular a self-cleaning microsparger arranged on the bottom of the tube and protruding into the mixture comprising the bacterial cells and the growth medium. Means for automatic acid and base supply for adjusting the pH of the mixture (7, 8) in particular include an inlet and a tube connected to peristaltic pumps (not shown).

Preferably, step a) comprises inoculating the fermenter with an inoculum comprising the bacterial cells and growth medium. In particular, the fermenter is inoculated with 10% (v/v) of the inoculum. The inoculum is preferably produced by mixing the bacterial cells with growth medium and incubating the culture under shaking conditions at about 250 rpm at a temperature of between about 15° C. and about 40° C. such as between about 30° C. and about 40° C., more preferably about 37° C. for at least about 8 h, preferably for at least about 10 h and in particular overnight.

"Growth medium" as known to one of skill in the art means a liquid comprising one or more substances that promote the growth of the bacterial cells such as terrific broth medium which composition is known to one of skill in the art.

The fermenter may further comprise one or more of and in particular all of:

an inlet for antifoam supply (9);

an outlet for exhaust gases (10) having a filter;

a pressure indicating unit such as a pressure gauge (11) in particular arranged on a top surface of the fermenter;

an overpressure valve (12) in particular connected to the pressure indicating unit on a top surface of the fermenter;

a sampling port (14) which may include a filter (13) and is in particular arranged on a top surface of the fermenter (opposite to the inlet for acid and base supply for adjusting the pH of the mixture and/or to the inlet configured for introducing the bacteria cells and the growth medium);

a dissolved oxygen sensor (15);

a pH sensor with integrated temperature sensor (16);

a control panel (17) in particular for commanding and controlling all required parameters including but not limited to the pH of the mixture and the dissolved oxygen saturation. The control panel can be connected to the dissolved oxygen sensor (15) and/or pH sensor with integrated temperature sensor (16). Signals from the dissolved oxygen sensor (15) and/or pH sensor with integrated temperature sensor (16) are integrated with the control panel from where, for example, pumps for acid and base supply will operate depending on the instructions received from the panel. For other parameters, values can be entered on the control panel and used for operation such as agitation at 3 Hz for moving the means for agitation at that value.

Step b) is preferably carried out at a frequency of about 3 Hz to about 5 Hz, more preferably at about 3 Hz and in particular at a temperature of about 37° C. and a pH of about 7.

The dissolved oxygen saturation is preferably about 30% saturation value in step b) and a constant air flow is provided by the means for air supply.

In particular the soluble oxygen is controlled at 30% saturation value by adjusting the agitation frequency and air flow. The pH is maintained between 6.5 and 7.5, in particular at about 7 by automatic addition of a base in particular NaOH or an acid in particular HCl by the means for automatic acid and base supply for adjusting the pH of the mixture (7, 8), in particular tubes automatically controlled by peristaltic pumps.

Preferably, the growth of the bacterial cells is determined during step b) by measuring optical density at about 600 nm such as every 1 h.

Step b) may be carried out for at least about 8 h, such as at least about 10 h and in particular overnight.

Step c) is preferably carried out by adding an inducer able to induce the production of the siRNA, in particular the expression of a siRNA precursor which can then be processed to siRNAs. The inducer is preferably IPTG (isopropyl beta-D-thiogalactoside). The inducer is preferably added in the exponential growth phase in particular in the mid exponential growth phase. "Mid-exponential growth phase" is known to one of skill in the art and means, for example, an optical density at 600 nm of about 10 in terrific broth medium.

In particular embodiments of the present invention, agitating the mixture in step b) is carried out with a frequency of about 3 Hz to about 5 Hz, at a temperature of about 37° C. and a pH of about 7 and a dissolved oxygen saturation of about 30%, wherein the dissolved oxygen saturation is controlled by adjusting the agitation frequency and air flow and the pH is maintained at about 7 by automatic addition of a base in particular NaOH or an acid in particular HCl by tubes automatically controlled by peristaltic pumps and wherein the expression of the siRNA is induced by adding isopropyl beta-D-thiogalactoside in mid exponential growth phase.

Step d) is preferably carried out for at least about 2 h, in particular for about 3 h.

The method of the present invention for producing siRNAs using a fermenter in step (ii) allows for producing siRNA with particular high yields such as of about 2 mg per liter of the bacterial cell culture within 2 days, reproducibly.

Preferably, the siRNA is isolated in step (iii) comprising steps of:

a) initiating lysis of the bacterial cells optionally after centrifuging the mixture;

b) centrifuging the lysate after step a) for obtaining a supernatant comprising the siRNA and a residue;

c) extracting and purifying the siRNA in the supernatant of step b) comprising contacting the supernatant with magnetic beads in particular magnetic nickel beads, more preferably magnetic Ni-NTA beads such as in form of a column, such as in commercially available systems like KINGFISHER™ Flex Purification System (Thermo Fisher Scientific) for affinity purification in particular of His-tagged polypeptides like the His-tagged p19 polypeptide or His-tagged p19 polypeptide bound siRNA and elution of siRNAs.

Lysis of the cells can be initiated by methods known to one of skill in the art. Cell lysis can, for example, be initiated by one or more of mechanical forces, enzymatic digestion, sonication, homogenization in homogenizers or freezing and grinding.

Lysis of the cells in step a) is preferably initiated by mechanical forces, in particular by adding a lysis buffer such as including phosphate buffer, NaCl, imidazole and triton X-100 with lysozyme and adding beads to the cells such as in commercially available beadbeaters for breaking cells by mechanical forces and releasing the cellular content.

Preferably, the eluate after step c) is subjected to anion exchange chromatography as step d) in particular in form of high-performance liquid chromatography (HPLC) for removing non-specifically bound polypeptides or other contaminants from the preceding purification step, in particular anion exchange chromatography is carried out with weak anion exchange magnetic beads or strong anion exchange (SAX) magnetic beads, most preferably with strong anion exchange (SAX) magnetic beads to remove RNAs larger than the size of the siRNA in particular with an elution buffer comprising NaCl. Non-limiting examples of elution buffers include elution buffers essentially consisting of about 0.1 to about 0.2 M NaCl. The anion exchange chromatography can be carried out in commercially available systems like the KINGFISHER™ Flex Purification System (Thermo Fisher Scientific) using SAX magnetic beads.

Preferably the eluate alternatively to or after step d) is contacted with solid phase reversible immobilization beads such as AMPure beads (Beckman Coulter) e.g. in commercially available systems like the KINGFISHER™ Flex Purification System (Thermo Fisher Scientific) to remove salts and other impurities as step e).

Figure 9:
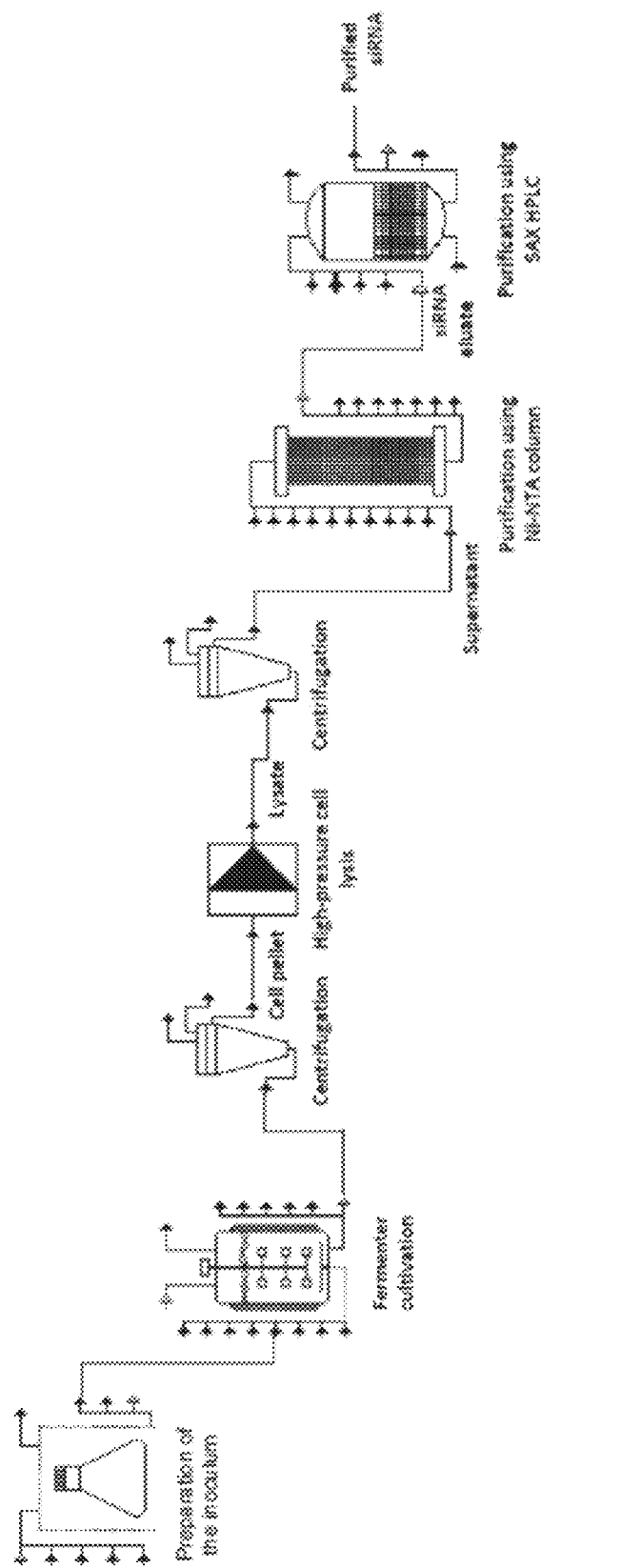
FIG. 9 is a schematic representation of an embodiment of a method of the present invention for siRNA production useful for industrial production of siRNAs.

FIG. 9 is a schematic representation of the siRNA production of the present invention and shows an embodiment for industrial production of siRNA comprising the inoculum preparation and inoculating the fermenter with an inoculum, agitating the mixture and inducing the production of siRNA and maintaining the bacterial cells in the mixture ("fermenter cultivation"), centrifuging the mixture for obtaining bacterial cell pellets, cell lysis by mechanical forces ("high pressure cell lysis"), centrifuging the lysate and subjecting the supernatant to Ni-NTA beads for extraction and purification for obtaining a siRNA eluate and subjecting the eluate to SAX HPLC for obtaining purified siRNA.

In another aspect, the present invention refers to a fermenter described above suitable for use for producing siRNA, in particular a fermenter (1) having an agitation unit (2) comprising means for agitation such as one or more impeller (3) and means for air supply into the mixture (4, 5) and having an inlet configured for introducing the siRNA expression system and/or growth medium (6), means for automatic acid and base supply for adjusting the pH of a mixture in the fermenter (7, 8) and a bioreactor vessel (19) into which in particular growth medium (20) and the siRNA expression system (21) can be introduced.

The agitation unit (2) in particular comprises means for agitation such as one or more impeller (3) and means for air supply into the mixture (4, 5) comprising a tube (5), a filter (18) and a microsparger (4), in particular a self-cleaning microsparger arranged on the bottom of the tube and able to protrude into a mixture introduced into the fermenter. Means for automatic acid and base supply for adjusting the pH of the mixture (7, 8) in particular include an inlet and a tube connected to peristaltic pumps (not shown).

The fermenter may further comprise one or more of and in particular all of:

an inlet for antifoam supply (9);

an outlet for exhaust gases (10) having a filter;

a pressure indicating unit such as a pressure gauge (11) in particular arranged on a top surface of the fermenter;

an overpressure valve (12) in particular connected to the pressure indicating unit on a top surface of the fermenter;

a sampling port (14) which may include a filter (13) and is in particular arranged on a top surface of the fermenter opposite to the inlet for acid and base supply for adjusting the pH of the mixture and/or to the inlet configured for introducing the siRNA expression system and/or growth medium;

a dissolved oxygen sensor (15);

a pH sensor with integrated temperature sensor (16);

a control panel (17) in particular for commanding and controlling all required parameters including but not limited to the pH of the mixture and the dissolved oxygen saturation. The control panel can be connected to the dissolved oxygen sensor (15) and/or pH sensor with integrated temperature sensor (16). Signals from the dissolved oxygen sensor (15) and/or pH sensor with integrated temperature sensor (16) are integrated with the control panel from where, for example, pumps for acid and base supply will operate depending on the instructions received from the panel. For other parameters, values can be entered on the control panel and used for operation such as agitation at 3 Hz for moving the means for agitation at that value.

Further provided by the present invention is a method of silencing a target gene in a cell population also referred to as "RNAi screen" by inducing degradation of target gene RNA expression products using the siRNA produced as described above comprising providing siRNA as described above from RNA isolated from a cell population and introducing said siRNA into said cell population.

The method of the present invention is in particular advantageous as the siRNA has been produced from siRNA expression systems obtained from RNA such as mRNA and non-coding RNA isolated from the same type of cell population into which the siRNA is introduced.

The method in particular further comprises introducing the cell population into multi-well plates, for example but not limited to 96 well plates or more with a density of, for example, but not limited to about 5,000 cells per well and adding siRNA to the wells. In particular, each well of the multi-well plate receives siRNA, in particular multiple siRNAs, produced from a different population of siRNA expression systems, in particular each well receives siRNA, in particular multiple siRNAs, specific for one gene. The concentration of the siRNA added may be, for example, about 2 nM.

The siRNA can be introduced into the cell population by methods known to a person of skill in the art for transfection such as microinjection, electroporation, and lipid-mediated transfection, in particular by adding a transfection reagent to the cell population such as a cationic liposome formulation like LIPOFECTAMINE™ such as LIPOFECTAMINE™ 2000 (Invitrogen).

The cell population is preferably incubated for at least about 12 h, in particular for about 24 h, i.e. maintaining the cell population under conditions favorable to transfection such as at a temperature of about 37° C. for a defined time period.

The method may further comprise a step of selecting cells into which the siRNA has been introduced.

Further, the method may comprise a step of determining the silencing efficiency of the target gene, in particular by determining the level of RNA expression products from said gene such as by means of qRT-PCR.

The target gene can be disease-associated. This means that an overexpression of the target gene is associated with the cause, progression, or maintenance of a disease, e.g. the target gene is an oncogene.

Silencing a target gene means an at least statistically significant inhibition of the expression of said target gene by degradation such as cleavage of its RNA expression products, in particular it means a decrease in said RNA expression products detectable with qRT-PCT by at least about 20%, further preferred by at least about 50% and in particular by more than 60% such as more than about 80% compared to a negative control without siRNA or with non-silencing siRNA such as siNC from GenePharma.

Still further provided is a method of identifying a functional target gene for treatment of a disease by using the siRNA produced as described above comprising:
(i) providing siRNA as described above from a siRNA expression system prepared with the RNA isolated from a cell population, which cell population is from a subject having a disease;
(ii) introducing the siRNA into the cell population;
(iii) analyzing the phenotype of the cell population.

The method of the present invention is in particular advantageous as the siRNA has been produced from siRNA expression systems in step (i) obtained from RNA such as mRNA or non-coding RNA isolated from the same type of cell population into which the siRNA is introduced in step (ii).

Step (ii) in particular further comprises introducing the cell population into multi-well plates, for example but not limited to 96 well plates or more with a density of, for example, but not limited to about 5,000 cells per well and adding siRNA to the wells. In particular, each well of the multi-well plate receives siRNA, in particular multiple siRNAs, produced from a different population of siRNA expression systems, in particular each well receives siRNA, in particular multiple siRNAs, specific for one gene. The concentration of the siRNA added may be, for example, about 2 nM.

The siRNA can be introduced into the cell population by methods known to a person of skill in the art for transfection such as microinjection, electroporation, and lipid-mediated transfection, in particular by adding a transfection reagent to the cell population such as a cationic liposome formulation like LIPOFECTAMINE™ such as LIPOFECTAMINE™ 2000 (Invitrogen).

Step (ii) preferably further comprises incubating the cell population for at least about 12 h, in particular for about 24 h, i.e. maintaining the cell population under conditions favorable to transfection such as at a temperature of about 37° C. for a defined time period.

The method may further comprise a step of selecting cells into which the siRNA has been introduced.

Step (iii) might include comparing the phenotype of the cell population with a negative control, i.e. a cell population of the same cell and tissue type without siRNA or in which non-silencing siRNA has been introduced such as siNC from GenePharma and/or a positive control of a cell population of the same cell and tissue type in which siRNA has been introduced which is known to influence the phenotype such as siRNA known to silence a specific gene influencing the phenotype of the cell population.

Step (iii) can include, for example, measuring the expression level of target genes in the cell population compared with a negative control.

Optionally step (iii) may include screening for a target gene based on the sequence of DNA coding for the siRNA whose phenotype has been found altered as the result of the phenotype analysis and/or determining the level of RNA expression products of the target gene by means of qRT-PCR.

The disease can be, for example, cancer, a viral disease or a genetic disease, in particular cancer. The cell population comprises and is in particular formed by cancer cells from a human. The cancer cells can be, for example, from a cervical cancer.

The target genes for treatment of a disease identified by the method can be treated either with the siRNA of the present invention and/or by other types of target gene-specific drugs e.g. small molecules, antibodies, gene editing techniques (Zinc finger nuclease, TALENs, CRISPR) and siRNAs made by other methods (e.g. chemical synthesis). In this case, the method of identifying a functional target gene for treatment of the present invention serves the purpose of a diagnostic tool for identifying therapeutic target genes for a disease.

The cell population comprises and is in particular formed by cancer cells as cell population and step (iii) then preferably includes determining the cell viability of said cell population such as with commercially available assays like the HCS VIABILITY ASSAY™, the CELLTITER-GLO™ Luminescent Cell Viability Assay (Promega) or flow cytometry and comparing the cell viability with a negative control, wherein a cell growth decreased to less than about 90%, in particular to less than about 60% compared to a negative control with siRNA non-specific for a gene from the cell indicates silencing of a gene that is essential for the growth of the cancer cells.

The cell population preferably comprises cancer cells and step (iii) includes determining the cell viability of the cell population, wherein a cell growth decreased to less than 60% compared to a negative control indicates silencing of a target gene that is essential for the growth of the cancer cells.

In another aspect, the present invention refers to a method of identifying RNAi therapeutics by using the siRNA produced as described above comprising:
(i) providing siRNA as described above from a siRNA expression system prepared with the RNA isolated from a cell population, in which the cell population harbors an increased expression or activity of a target gene indicative of a certain disease;

(ii) introducing the siRNA into the cell population;

(iii) determining the silencing efficiency comprising determining the level of RNA expression products of said target gene in particular by means of qRT-PCR.

The method of the present invention is in particular advantageous as the siRNA has been produced from siRNA expression systems in step (i) obtained from RNA such as mRNA and non-coding RNA isolated from the same type of cell population into which the siRNA is introduced in step (ii).

An "increased expression" or "increased activity" can be due to a mutation in the target gene. Increased activity or increased expression in particular means significantly increased, in particular at least 10% and further preferred at least 30% increase in the expression or activity of the target gene which can be determined with methods known to one of skill in the art including Western blotting or the like.

Step (ii) in particular further comprises introducing the cell population into multi-well plates, for example but not limited to 96 well plates or more with a density of, for example, but not limited to about 5,000 cells per well and adding siRNA to the wells. In particular, each well of the multi-well plate receives siRNA, in particular multiple siRNAs, produced from a different population of siRNA expression systems, in particular each well receives siRNA, in particular multiple siRNAs, specific for one gene. The concentration of the siRNA added may be, for example, about 2 nM.

The siRNA can be introduced into the cell population by methods known to a person of skill in the art for transfection such as microinjection, electroporation, and lipid-mediated transfection, in particular by adding a transfection reagent to the cell population such as a cationic liposome formulation like LIPOFECTAMINE™ such as LIPOFECTAMINE™ 2000 (Invitrogen).

Step (ii) preferably further comprises incubating the cell population for at least about 12 h, in particular for about 24 h, i.e. maintaining the cell population under conditions favorable to transfection such as at a temperature of about 37° C. for a defined time period.

The method may further comprise a step of selecting cells into which the siRNA has been introduced.

In particular, an at least about 50%, preferably at least about 60% and in particular at least about 80% decrease in the level of RNA expression products of the target gene compared to a negative control indicates that the siRNA is a potential RNAi therapeutic against said target gene.

The siRNA as RNAi therapeutic can be used for treatment of a subject such as an animal or a human. I.e. the present invention further provides a method for treating of a subject suffering from a disease comprising administering an effective amount of a siRNA identified as RNAi therapeutic according to the method described above to the subject. As a non-limiting example, the disease can be, for example, cancer, a viral disease or a genetic disease. The subject is in particular a human or an animal. siRNA can be administered in form of a pharmaceutical comprising which can be in liquid, semi-solid or solid form further comprising at least one pharmaceutically tolerable excipient like a pharmaceutically tolerable carrier, filler, solvent, diluent and the like. In particular, the siRNA can be packaged into delivery vehicles suitable for in vivo delivery such as in lipid-based and polymer-based nanoparticles. The siRNA may be administered to the subject by an oral or parenteral route.

The method of the present invention of silencing a target gene in a cell population, of identifying a functional target gene for treatment of a disease and of identifying RNAi therapeutics can utilize any method for analyzing the phenotype of the cell population and determining the silencing efficiency, wherein determining cell growth and cell viability represents only one example in particular suitable in case the cell population is of cancer cells. Indications and parameters suitable for any disease or biological process could be applied.

A person of skill in the art will understand that the particular advantage of the present invention is obtained by combining the methods of the present invention wherein the skilled person will appreciate that the invention includes all combinations of steps and features referred to or indicated in the specification, individually or collectively, and any and all combinations of the steps or features for each method.

A preferred embodiment of a method for the integrated production of a library of siRNA expression systems prepared from RNA isolated from a cell population, production of siRNA from said library, determination of silencing of a target gene in said cell population such as by determining the phenotype or level of RNA expression products from said target gene compared to a negative control and/or a positive control and production of one or more siRNA species leading to a predetermined phenotype and/or predetermined silencing efficiency in particular by using a fermenter of the present invention. Hence, the present invention further relates to a method for producing siRNA leading to a predetermined phenotype and/or predetermined silencing efficiency for a target gene comprising steps of:

A) preparing a library of small interfering RNA (siRNA) expression systems comprising isolating RNA from a cell population from a subject with a disease such as cancer; generating RNA fragments from the isolated RNA; converting the RNA fragments into dsDNA fragments; cloning the dsDNA fragments into vectors, each vector comprising one or more promoters and at least one restriction enzyme site capable of accepting the insertion of at least one dsDNA fragment such that siRNA can be produced, and transforming the vectors into bacterial cells;

B) producing siRNA from the siRNA expression system of step A) comprising subjecting the bacterial cells to conditions under which siRNA is produced and isolating the siRNA; in particular step B) comprises introducing the bacterial cells into micro-well plates in particular such that one well receives one population of bacterial cells; subjecting the micro-well plates to conditions under which the bacterial cells grow, and inducing siRNA production; wherein isolating the siRNA in particular comprises initiating lysis of the bacterial cells such as by mechanical forces; centrifuging the lysate for obtaining a supernatant comprising the siRNA and a residue; extracting and purifying the siRNA in the supernatant comprising contacting the supernatant with magnetic beads for affinity purification and elution of siRNAs, subjecting the eluate to anion exchange chromatography with strong anion exchange magnetic beads and/or solid phase reversible immobilization beads;

C) silencing a target gene in the cell population comprising introducing the siRNA into the cell population, analyzing the phenotype of the cell population and/or determining the silencing efficiency comprising determining the level of RNA expression products from said target gene; in particular step C) comprises introducing the cell population into multi-well plates such that each well of the multi-well plate receives siRNA produced from a different population of bacterial cells, in particular each well receives siRNA specific for one gene and analyzing the phenotype of the cell population such as the cell viability for example by means of HCS or CTG and/or determining the silencing efficiency comprising determining the level of RNA expression products from said gene; step C) may further comprise sequencing the siRNA or dsDNA fragment in the cloned vector to identify the target gene;

D) selecting the siRNA leading to a predetermined phenotype and/or having a predetermined silencing efficiency and producing siRNA from bacterial cells prepared according to step A) which are able to produce said siRNA comprising subjecting the bacterial cells to conditions under which the siRNA is produced and isolating the siRNA for further RNAi screen, wherein step D) in particular includes introducing a mixture comprising the bacterial cells and growth medium in a fermenter (1) having an agitation unit (2) comprising means for agitation (3) and means for air supply into the mixture (4, 5) and having an inlet configured for introducing the siRNA expression system (6) and means for automatic acid and base supply for adjusting the pH of the mixture (7, 8); agitating the mixture at a temperature between about 15° C. and about 40° C. such as between about 30° C. and about 40° C. and a pH of between about 6.5 and about 7.5; inducing the expression of siRNA; and maintaining the bacterial cells in the mixture for at least about 1 h under conditions under which the bacterial cells grow; and wherein isolating the siRNA in particular comprises initiating lysis of the bacterial cells such as by mechanical forces; centrifuging the lysate for obtaining a supernatant comprising the siRNA and a residue; extracting and purifying the siRNA in the supernatant comprising contacting the supernatant with magnetic beads for affinity purification and elution of siRNAs, subjecting the eluate to anion exchange chromatography with strong anion exchange magnetic beads followed by contacting the eluate with solid phase reversible immobilization beads.

Figure 10:
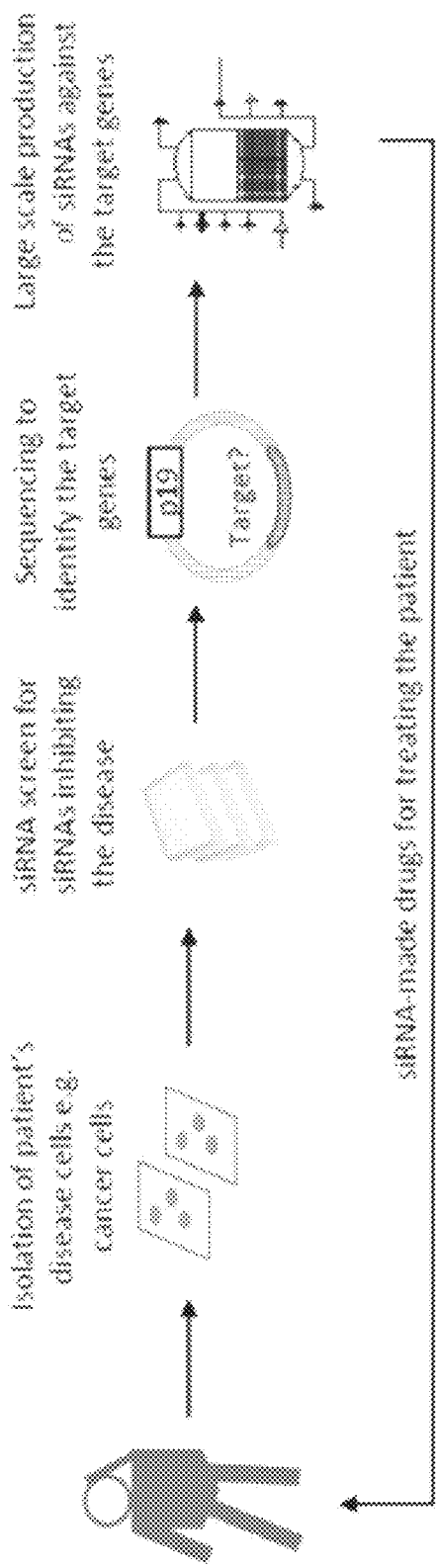
FIG. 10 is a schematic representation of an integrated method for producing a library of siRNA expression systems, for producing siRNA, for RNAi screen and for large scale production of a siRNA candidate with advantageous RNAi.

FIG. 10 shows an embodiment of such integrated method comprising obtaining a cell population such cancer cells from a patient, preparing a siRNA expression system from the RNA isolated from said cell population, preparing siRNA from said expression system, silencing target genes with said siRNA in the same type of cell population including identifying functional target genes for treatment of the disease, sequencing to identify the target genes and producing siRNA using a fermenter as described above.

EXAMPLES

Example 1A

Preparing a Transcriptome-Wide Library of siRNA Expression Systems from HeLa Cancer Cells According to the Present Invention The overall strategy of the siRNA library preparation and RNAi screen method is outlined in FIG. 1. Total RNA is from a certain target cell line and then converted into a dsDNA library inside a siRNA producing plasmid.

Figure 3A:
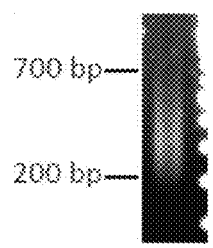
FIG. 3A is an image of a SYBR™ Green agarose gel stain showing the size of dsDNA fragments after adaptor ligation and PCR enrichment.
Figure 3B:
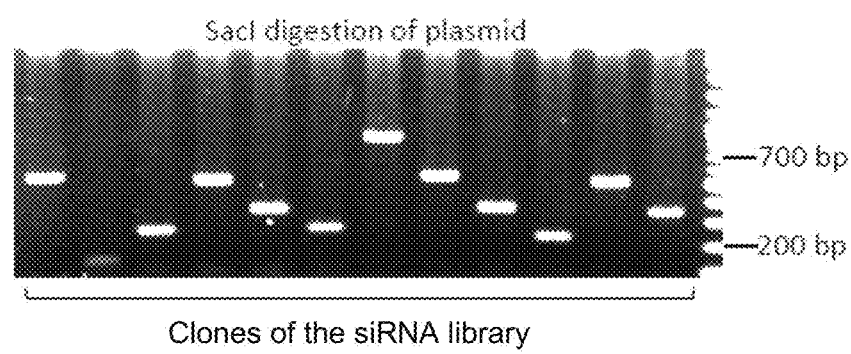
FIG. 3B shows the gel image after a digestion test by SacI of cloned plasmids with dsDNA fragments.

Total RNAs from HeLa-d1EGFP (HeLa cells with a EGFP transgene) were firstly extracted followed by ribosome RNA removal. RNA was fragmented into smaller pieces of ~200 nucleotides to ~700 nucleotides, and then converted into dsDNA fragments. The dsDNA fragments were then ligated via TA cloning method to a specially designed adaptor containing SacI restriction site (FIG. 2A) which matches the restriction site on the plasmid. The dsDNA fragments were then amplified by PCR (using a primer matching the adaptor), digested by SacI and finally ligated to the vector. FIG. 3A shows the DNA fragments after SacI adaptor ligation and PCR. In this case the size range of the dsDNA fragments was from ~200 nucleotides to ~700 nucleotides, which are suitable for cloning into the plasmid. After dsDNA fragments ligation to the plasmid, a digestion test was performed on plasmids extracted from several independent clones (FIG. 3B). High ligation efficiency could be achieved (100% in this case) and the size range of dsDNA insertions was similar to the size range of the dsDNA fragments before ligation.

Figure 3C:
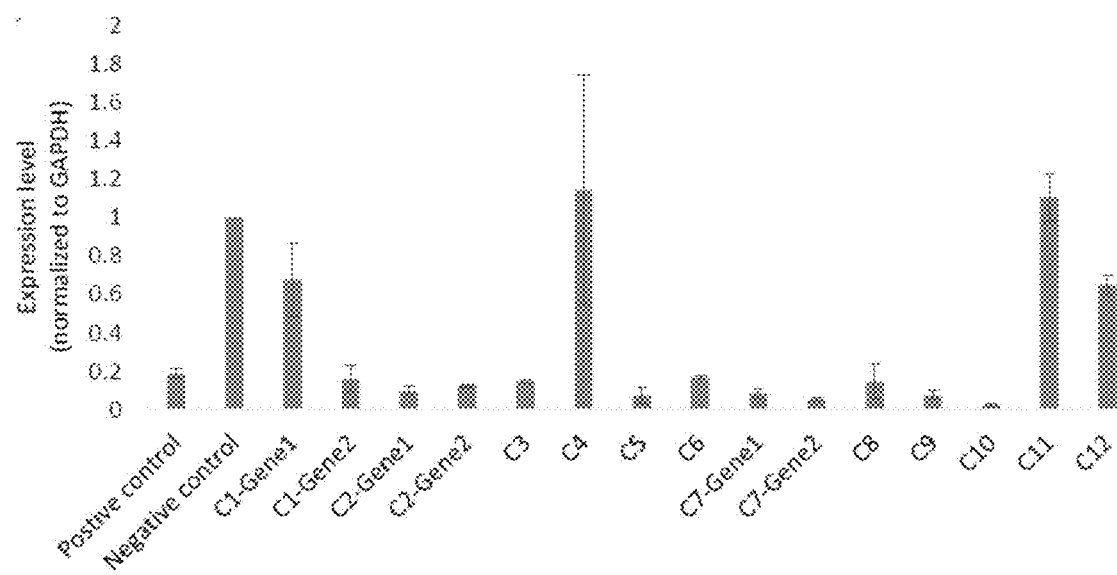
FIG. 3C is a bar chart showing the silencing efficiency of target genes using siRNAs produced from a library of siRNA expression systems of the present invention, namely cloned plasmids of 12 clones (see Table 1). A high percentage of siRNAs (11 out of 15) were able to suppress the corresponding target gene to <20% compared to the level in the negative control sample.

Twelve clones, i.e. populations of twelve cloned plasmids have been chosen to sequence the plasmid to identify the inserted dsDNA fragments (Table 1). And the results showed that the twelve clones cover a diverse range of fourteen unique genes. Interestingly three of the clones, C1 C2 and C7, contain two different gene fragments (referred as "Gene1" and "Gene2" in Table 1 and in FIG. 3C) suggesting multiple dsDNA fragments can ligate together before insertion into the plasmid since the DNA fragments contain the same restriction site at both ends. Thus one siRNA plasmid could potentially produce siRNAs targeting more than one gene.

TABLE 1

Sequencing results of 12 siRNA library clones

| Clone ID | Multiple gene | Target gene |
| --- | --- | --- |
| C1 | Gene1 | *Homo sapiens* pleckstrin homology domain containing, family G (with RhoGef domain) member 3 (PLEKHG3) |
|  | Gene2 | *Homo sapiens* transducin (beta)-like 1X-linked (TBL1X), transcript variant 4 |
| C2 | Gene1 | *Homo sapiens* cirrhosis, autosomal recessive 1A (cirhin) (CIRH1A) |
|  | Gene2 | *Homo sapiens* G protein-coupled receptor kinase interacting ArfGAP 1 (GIT1), transcript variant 1 |
| C3 |  | *Homo sapiens* v-ski avian sarcoma viral oncogene homolog (SKI) |
| C4 |  | *Homo sapiens* filamin A, alpha (FLNA), transcript variant 2 |
| C5 |  | *Homo sapiens* filamin A, alpha (FLNA), transcript variant 2 |
| C6 |  | *Homo sapiens* ubiquitin C (UBC) |
| C7 | Gene1 | *Homo sapiens* peroxidasin (PXDN) |
|  | Gene2 | *Homo sapiens* parathymosin (PTMS) |
| C8 |  | *Homo sapiens* casein kinase 1, alpha 1 (CSNK1A1), transcript variant 4 |
| C9 |  | *Homo sapiens* H19, imprinted maternally expressed transcript (non-protein coding) (H19) |
| C10 |  | *Homo sapiens* prothymosin, alpha (PTMA), transcript variant 2 |
| C11 |  | *Homo sapiens* ubiquitin specific peptidase 10 (USP10), transcript variant 4 |
| C12 |  | *Homo sapiens* TAF5-like RNA polymerase II, p300/CBP-associated factor (PCAF)-associated factor, 65 kDa (TAF5L), transcript variant 1 |

Example 1B

Silencing Efficiency of the siRNAs Produced from the siRNA Expression Systems

To test the silencing efficiency of the siRNAs produced using the siRNA library production method, siRNAs have been extracted from the twelve individual clones. Purified siRNAs (according to Huang and Lieberman, Nat Protoc, 2013, 8(12):2325-36) were transfected into HeLa-d1EGFP cells and qRT-PCR was performed to test the RNA silencing efficiency. The results (FIG. 3C) showed more than 80% knockdown of the target gene in 11 out of the 15 tests. These results demonstrate that a high percentage of siRNA library clones (>70%) can produce highly efficient siRNAs targeting their corresponding target genes, i.e. cleaving the corresponding RNA. Furthermore, for C2 and C7 the siRNAs can suppress both target genes proving that one siRNA library plasmid, if it contains multiple dsDNA fragments, i.e. multiple gene fragments, could produce siRNAs that can simultaneously suppress multiple genes.

In summary these data demonstrate that the siRNA library production method of the present invention method has successfully created cell line specific siRNA libraries that are "personalized" to the cells' transcriptome and can produce highly efficient siRNAs targeting the corresponding genes by cleaving RNA.

Example 1C

Production of siRNA from a Library of siRNA Expression Systems According to the Present Invention In order to cover the entire transcriptome of the target cell, the number of siRNA needed to be produced is in the thousands range. A high-throughput bacteria culture and siRNA isolation method has been created for the purpose of producing siRNA libraries containing thousands of individual siRNA expression systems (FIG. 4).

The siRNA library plasmid was firstly transformed into *E. coli* cells capable of supporting siRNA production. After overnight incubation at 37° C. on culture medium with antibiotic selection, individual clones were then inoculated into a well of 96 deep well plate pre-added with 1 ml culture medium. Each well the contained one unique dsDNA fragment of a specific sequence cloned in a vector. Thus each 96 well plate could produce 96 individual siRNAs. Multiple plates were prepared in the same manner to reach the number of thousands siRNAs. The plate was then sealed with a breathable film and placed into an incubator shaker for cultivation for up to 21 hours with vigorous shaking. siRNA production has been induced by adding IPTG when the bacteria were in the exponential growth phase. Before the isolation of siRNAs, a small proportion of the bacterial cells were saved in glycerol solution and stored at −80° C. The bacterial glycerol stock was used for sequencing the DNA insert and for later isolation of the siRNAs.

After the bacterial culture step, the cells were lysed in lysis buffer by a beadbeater, which broke cells by mechanical forces and then released the cellular content. The plate was centrifuged at high speed and then the supernatant was transferred into another 96 well plate for siRNA purification using magnetic beads. KINGFISHER™ Flex Purification System (Thermo Fisher Scientific) was used for high-throughput and automated siRNA purification.

Figure 5A:
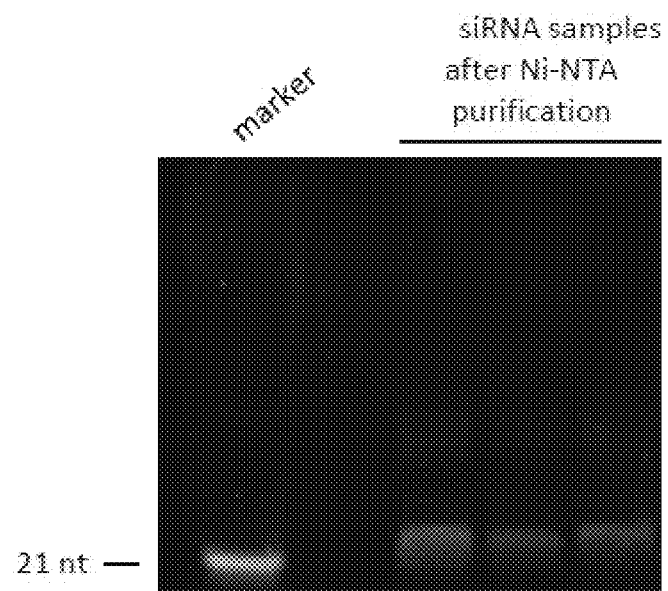
FIG. 5A is an image of a SYBR™ Gold polyacrylamide gel stain showing siRNA samples purified with Ni-NTA magnetic beads by KINGFISHER™ Flex Purification System.
Figure 5B:
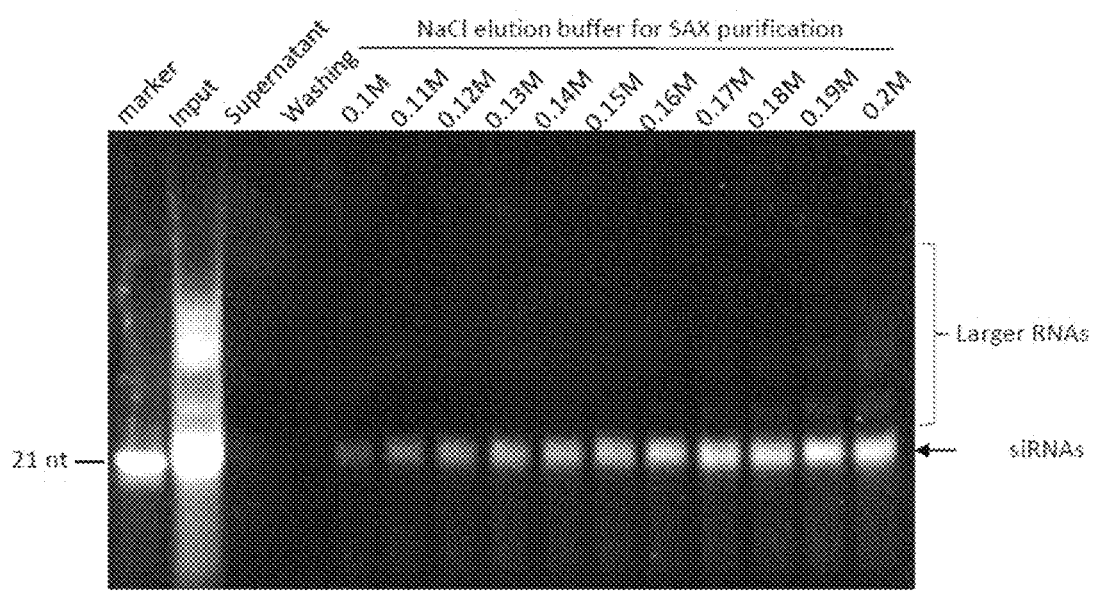
FIG. 5B is an is an image of a SYBR™ Gold polyacrylamide gel stain showing siRNA samples isolated using SAX magnetic beads with 0.1 to 0.2 M NaCl as elution buffer by KINGFISHER™ Flex Purification System.
Figure 5C:
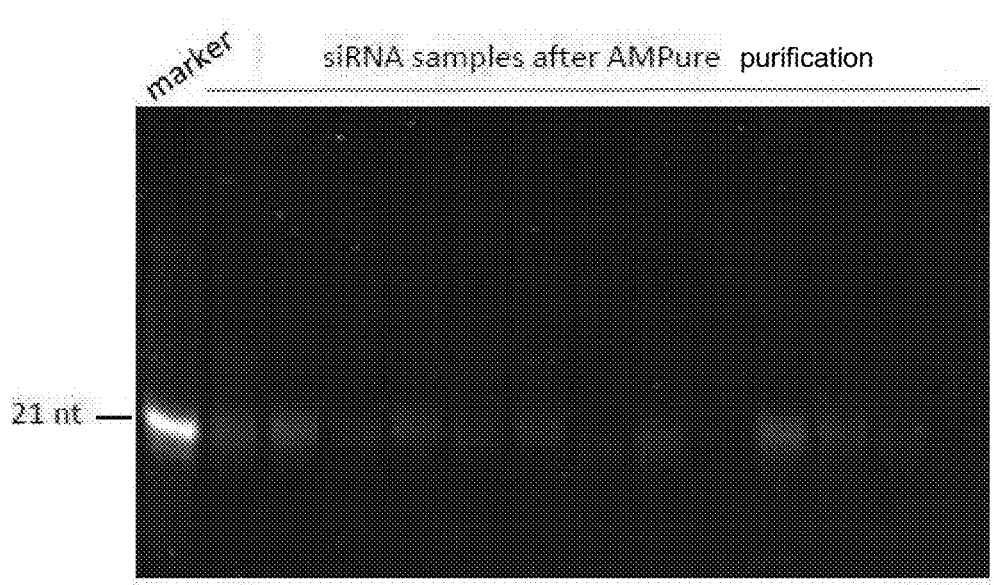
FIG. 5C is an image of a SYBR™ Gold polyacrylamide gel stain showing the influence of further purification and desalting of siRNAs using AMPure magnetic beads by KINGFISHER™ Flex Purification System.

The first round of purification included binding to magnetic nickel beads, multiple washing and elution steps. FIG. 5A shows several individual siRNA samples extracted using magnetic Ni-NTA beads in a 96 well plate by the KING-FISHER™ Flex Purification System. A further purification step was anion exchange purification using strong anion exchange (SAX) magnetic beads to remove RNAs larger than the size of siRNA (~21 bp). For the anion exchange purification, FIG. 5B shows that using a solution of −0.15 M NaCl in the elution step retrieved siRNA of mainly around ~21 bp. The final step was to use solid phase reversible immobilization beads in form of AMPure beads (Beckman Coulter) to remove salts and other impurities from siRNA. The purified siRNAs were then in a solution of nuclease-free water, ready for use in downstream applications. FIG. 5C shows a few such individual siRNAs purified after the AMPure beads purification in 96 well format using the KINGFISHER™ Flex Purification System.

The bacterial culture and isolation process has been repeatedly performed in 96 well plate in order to produce thousands of siRNAs. The siRNAs purified using the above method showed a predominant band at around 21 bp (FIGS. 5C and 5D) proving the high efficiency and high purity achieved by the method for preparing siRNA from the library of siRNA expression systems of the present invention.

Example 1D

Identifying Functional Genes in Cancer Cells with the siRNA Produced from the Library of siRNA Expression Systems of the Present Invention Using the above approaches, a siRNA library allowing for the production of 960 individual siRNAs derived from RNAs isolated from HeLa-d1EGFP cells has been provided. To demonstrate the utility of the siRNA library, a siRNA screen for identifying functional genes required for cancer cell survival in HeLa-d1EGFP cells has been performed. The genes identified from this type of RNAi screen could potentially become therapeutic targets for cancer.

HeLa-d1EGFP cells were plated into 96 well plates at a density of 5,000 cells per well. After the cells were attached to the plate, 10 ul of siRNA from one well obtained from the library of siRNA expression systems were transfected into one well of the cells using LIPOFECTAMINE™ 2000 (Invitrogen). After 24 hours of transfection, the number of live cells in each well, which positively correlates with cell viability, was measured. siRNAs against PLK1 (siPLK1 GenePharma, sequence: SEQ. ID. No:3), a known gene essential for cancer cell division, were used as the positive control (which will cause markedly decrease in cell viability). Negative control siRNAs (siNC; NC siRNA, B01001, GenePharma), ordered from GenePharma company, were used as the negative control of the screen.

Figure 6A:
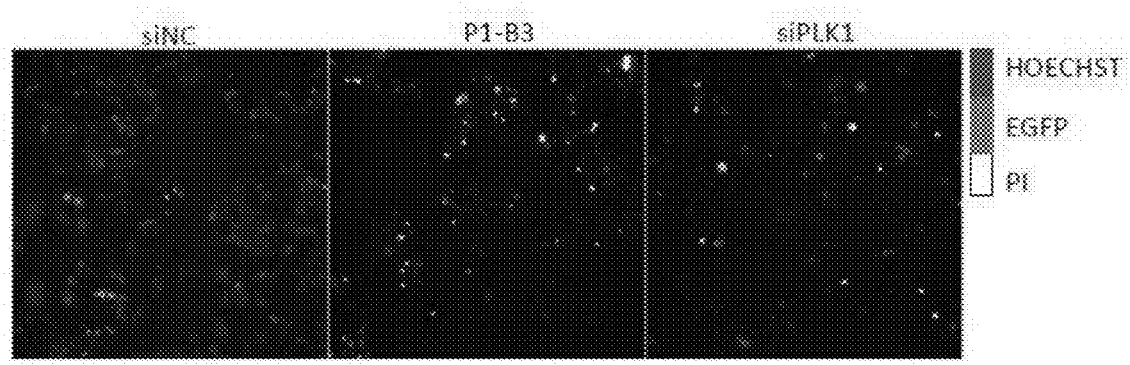
FIG. 6A shows imaging results for representative wells of HeLa cancer cells transfected with siRNA together with the positive control siPLK and the negative control siNC. HeLa cells were co-stained with Hoechst 33342 (Life Technologies) and Propidium Iodide (PI, Life Technologies) for 10 minutes and then placed into the HCS machine to collect microscopic images for Hoechst, PI and EGFP channels. Merged color images under the condition of 10× objective. Blue dots indicate cell nucleus stained by HOECHST 33342 (live cells); green dots indicate EGFP-Hela cells; white dots indicate cell nucleus stained by PI (dead cells). From left to right are representative fields from siNC, Plate 1 Well B3 (P1-B3) siRNA and siPLK1.

Two rounds of siRNA screen were performed using two different readouts for the number of live cells. The first one was using a CellInsight CX7 High Content Screen (HCS) Platform (Thermo Fisher Scientific). For the HCS method, cells were co-stained with Hoechst 33342 (Life Technologies) and Propidium Iodide (PI, Life Technologies) for 10 minutes and then placed into the HSC machine to collect microscopic images for Hoechst, PI and EGFP channels. Representative data from one screened well of cells transfected with a siRNA, together will positive control (siPLK1) and negative control (siNC) wells, are shown in FIG. 6A. In this case, Well P1-B3 showed a significantly reduced number of viable cells comparing to the negative control.

Figure 6B:
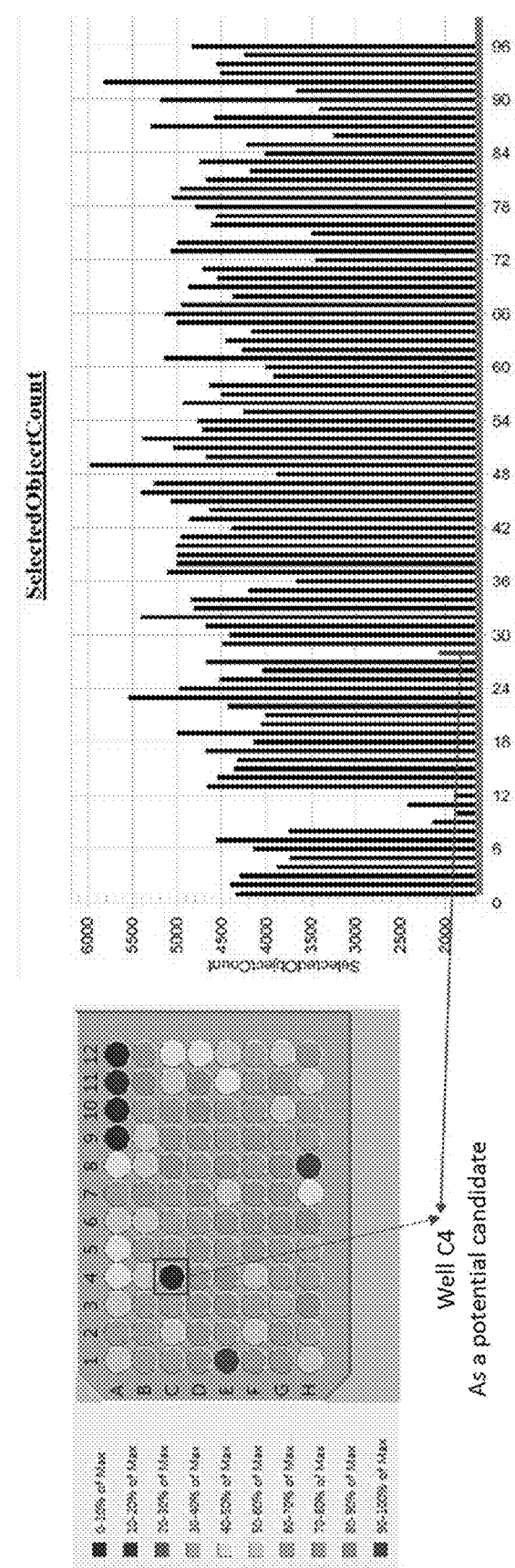
FIG. 6B shows an image of the multi-well plate and an example for data collection and the auto-analysis by CellInsight CX7 High Content Screening (HCS) Platform. "Selected Object Count" represents the total number counted from cells with only HOECHST stained which indicates live cells. The bar chart diagram on the right shows a relative percentage of live cells. siNC was transfected in four replicates from Well A1 to Well A4 as a negative control for normalization in cell viability test in each screen plate. siPLK1 was transfected in four replicates from Well A9 to Well A12 as a positive control in each screen plate.

Parameters for the HCS software have been devised to automatically analyze the images and calculate total number of viable cells in each well. Then wells which showed similar viable cell counts have been chosen comparing to the wells treated with positive control siPLK1, as the potential candidate. Analyzed results from one of the 96 well plates showed that siRNAs from well C4 caused significant reduction in live cell number (FIG. 6B). In the end C4 was selected among the candidate pro-siRNAs which could severely impair cancer cell survival.

Figure 6C:
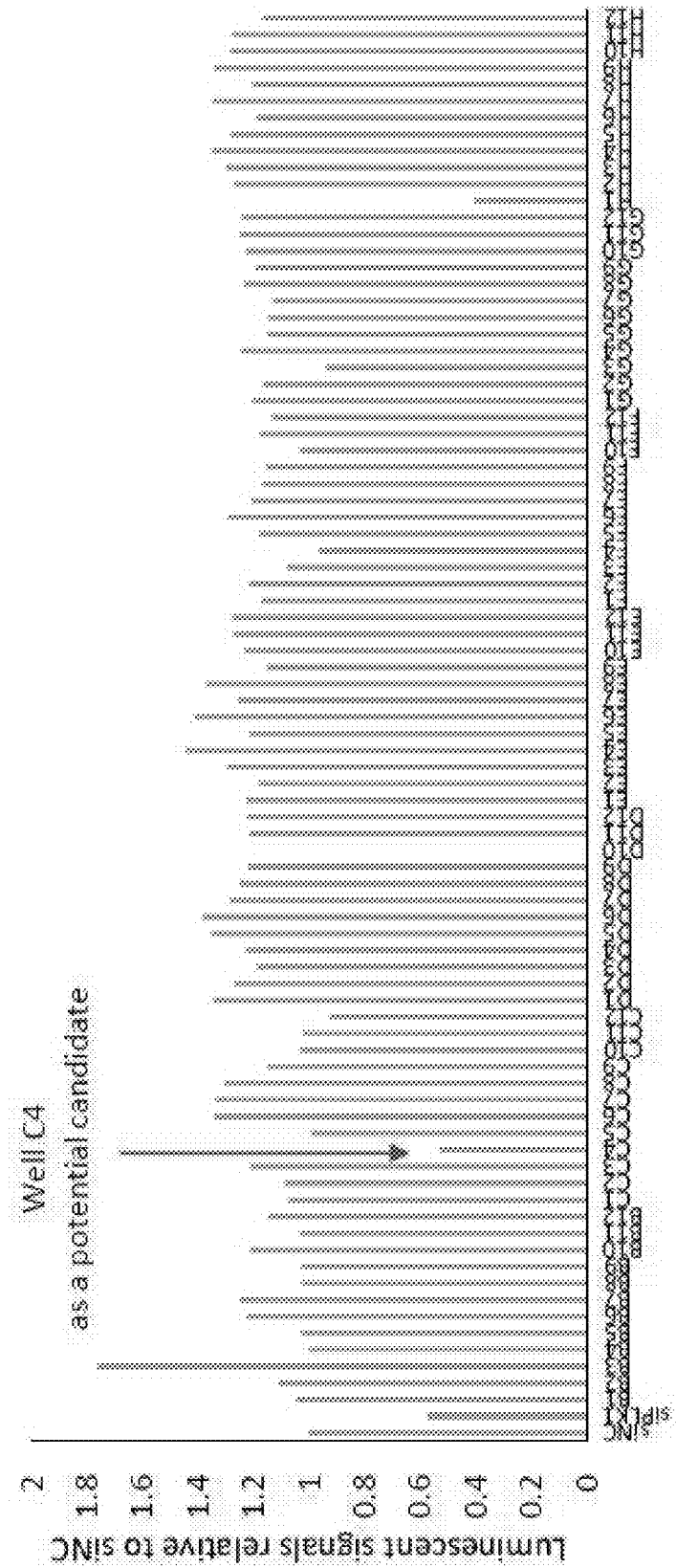
FIG. 6C shows exemplary data for a cell viability assay using CELLTITER-GLO™ (CTG) for the same 96 well plate as in FIG. 6B. Data for siNC are the first column and data for siPLK1 are the second column.
Figure 7A:
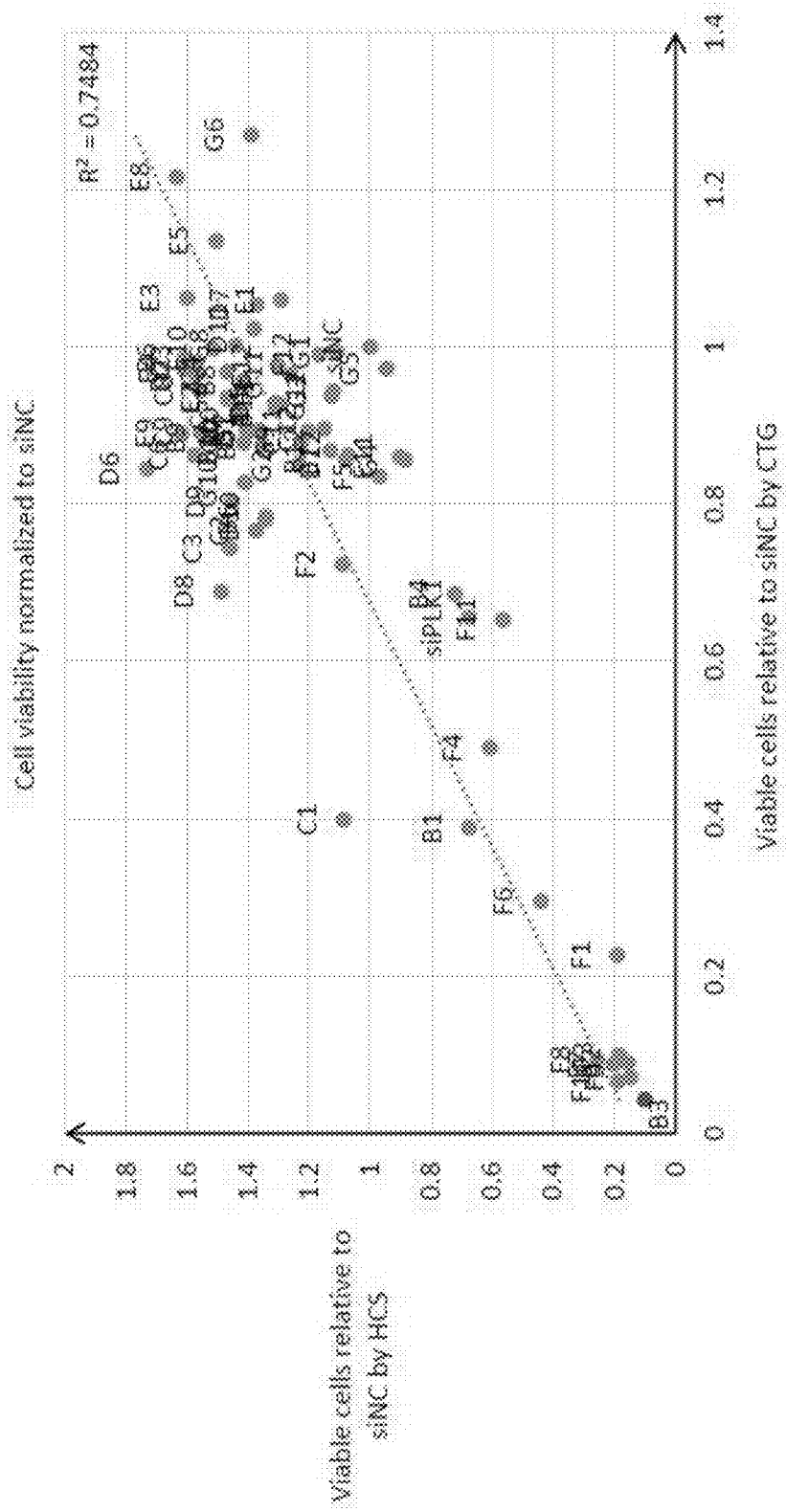
FIG. 7A shows a correlation between HCS and CTG datasets from one of the 96 well screen plates. X axis, viable cell data relative to siNC from CTG assay. Y axis, viable cell data relative to siNC from HCS assay. Red dot is the data from PHGDH siRNA. Datasets obtained from both screen methods correlate relatively well with each other. Linear regression trend line and its $R^2$ value are shown.

For the second round of screen, cell viability was monitored by the CellTiter-Glo (CTG) Luminescent Cell Viability Assay (Promega). The luminescent signals, which positively correlate with the number of live cells, were read by a microplate reader (BioTek). The data from siRNA transfected samples were normalized to siNC transfected negative control samples for both HCS and CTG screen datasets. A representative dataset using CTG assay for a 96 well screen plate is shown in FIG. 6C. The results from CTG assay were then compared with the results obtained by HCS method and the two datasets generally agreed with each other (FIG. 7A).

Figure 7B:
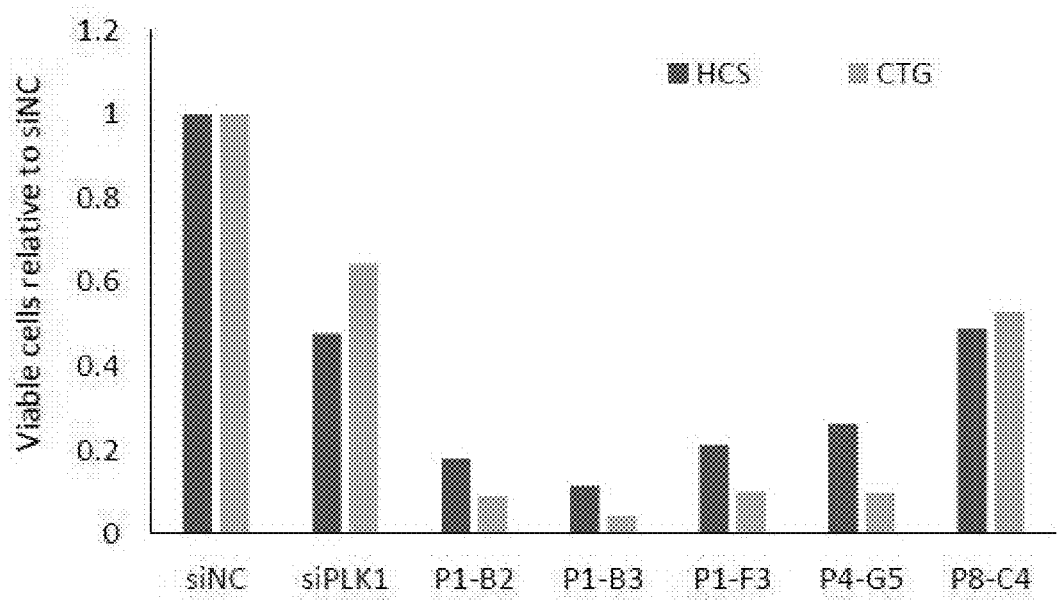
FIG. 7B is a bar chart diagram showing the results of the five candidate siRNAs that consistently decreased cell viability to less than 60% (relative to siNC control) in both HCS and CTG assays. Their target genes are given in Table 2. siPLK1 data are also shown.

From the eleven 96 well screen plates, five siRNA candidates have been selected that consistently decreased cell viability to less than 60% comparing to negative control in both HCS and CTG assays (FIG. 6B, 6C and FIG. 7B). The glycerol stocks of these siRNA clones have been retrieved, the cloned plasmids extracted and sequenced to identify the target genes. The sequencing results showed that those five cloned plasmids contain five different genes or genomic sequences (Table 2). Interestingly one of the candidates, phosphoglycerate dehydrogenase (PHGDH) was identified by a previous RNAi screen as an essential metabolic gene for human breast cancer (Possemato et al, Nature. 2011 Aug. 18, 476(7360):346-50). The fact that the method of the present invention was able to identify the same candidate as the other RNAi screen proves that the methods of the present invention can identify authentic players in a certain biological pathway.

The methods of the present invention can also be applied to functional genomic studies for other cancer types and other diseases.

expression strain with siRNA expression plasmid. For inoculum preparation, the recombinant strain has been grown overnight at 37° C. in a 1 L baffled flask containing 100 mL optimized growth medium in an orbital shaker incubator rotating at 250 rpm. The fermenter is inoculated with 10% (v/v) inoculum. Agitation in fermenter is initially set at frequency (3 Hz). Temperature is controlled at 37° C. while pH is maintained at 7.0 by automatic addition of NaOH or HCl through feeding tubes automatically controlled by peristaltic pumps. Dissolved oxygen (DO) is controlled at 30% saturation value by increasing agitation frequency (3-5 Hz) and air flow if required. A constant air flow is applied through a self-cleaning microsparger mounted at the bottom of the agitation unit. Samples are aseptically withdrawn every 1 h from the fermenter to measure the optical density (OD) at 600 nm for monitoring bacterial growth. IPTG induction in the fermenter is done when the culture is in mid-exponential phase and the culture is allowed to grow further for another 3 h. Subsequently the culture is harvested and bacterial pellet is stored at −80° C. until siRNA isolation.

The optimized large scale siRNA isolation method started with cell lysis using a high-pressure based method to enable efficient processing of large bacterial culture pellet obtained from the fermenter. This was followed by highly stringent binding and washing steps to remove the non-specifically bound proteins and other contaminants from Nickel-NTA affinity beads. Finally, siRNAs were eluted under optimal shaking conditions to ensure its complete elution the Ni-NTA beads. To get pure siRNAs with no contaminating longer RNAs, an optimized HPLC purification using anion exchange column (using either weak anion exchanger or strong anion exchanger) has also been developed.

With the optimized large scale production and purification method of the present invention, siRNAs can be produced at around 2 milligrams per litre scale very quickly (within 2 days) and reproducibly. FIG. 8B shows the results from fermenter-based siRNA production compared to conven-

TABLE 2

Candidate siRNAs that affect cancer cell viability.

| No. | Plate No. | Well No. | Insert Size | Target gene |
|---|---|---|---|---|
| 1 | P1 | B2 | 284 | Muscleblind like splicing regulator 1 (MBNL1), RefSeqGene on chromosome 3 |
| 2 | P1 | B3 | 458 | Phosphoglycerate dehydrogenase (PHGDH), mRNA |
| 3 | P1 | F3 | 136 | Chromosome X, alternate assembly CHM1_1.1, transmembrane protein 164 |
| 4 | P4 | G5 | 676 | G protein subunit alpha 13 (GNA13), CDS variant 1, mRNA |
| 5 | P8 | C4 | 339 | Chromosome 8, alternate assembly CHM1_1.1, SH2 domain containing 4A |

Example 2

Method for Producing Large Amounts of siRNAs from the Library of siRNA Expression Systems Once potential functional target genes have been identified, they need to be functionally validated in in vitro and in vivo experiments. For in vivo experiments in animal and for therapeutic applications, large amounts of siRNAs would be required. Thus, a method for large scale production of siRNAs has been developed and optimized.

Figure 8A:
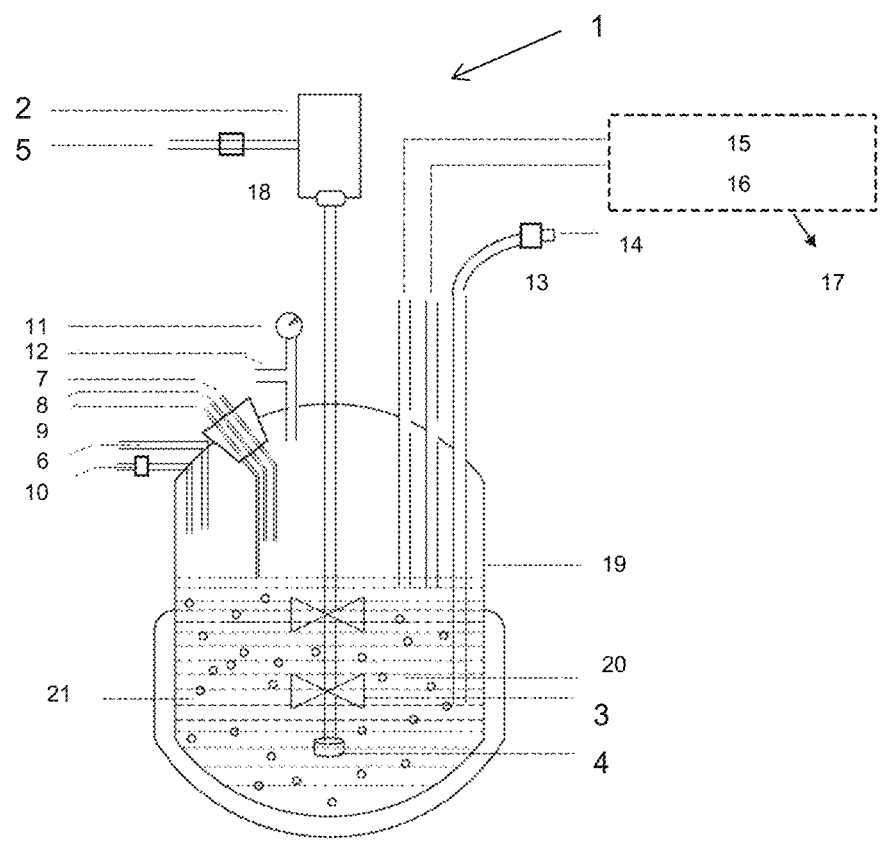
FIG. 8A is a schematic representation of a fermenter of preferred embodiments of the present Invention.
Figure 8B:
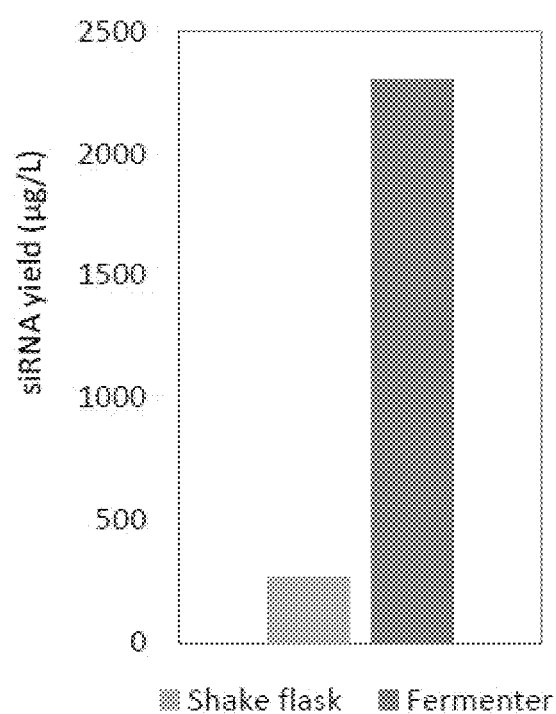
FIG. 8B is a bar chart diagram showing a yield comparison between conventional laboratory methods (shake flask) and the method of the present invention using a fermenter.

The large scale siRNA production method has been developed based on a fermenter system (a schematic of a fermenter for siRNA production is shown in FIG. 8A). The production is initiated with the transformation of E. coli T7 tional laboratory production method (shake flask method). An almost 10-fold improvement in the siRNA yield using optimized large scale production method in the fermenter is achieved with the method of the present invention compared to the shake flask method.

To summarize, an optimal method for large scale production and isolation of highly pure pro-siRNAs has been provided with the present invention. This development further adds merit to the novel method for preparing a library of siRNA expression systems and producing siRNA therefrom for RNAi screen for identifying functional target genes by facilitating the functional validation of identified target genes in vivo and by enabling bulk production of siRNAs. This method can be easily adapted to an industrial setting.

FIG. 9 gives a schematic presentation of a setup for large scale production applied and extraction and purification of siRNAs in an industrial fermentation facility.

LIST OF REFERENCE SIGNS

1 Fermenter
2 Agitation unit
3 Means for agitation such as one or more impeller
4 Means for air supply into the mixture, e.g. microsparger
5 Means for air supply into the mixture, e.g. tube
6 Inlet suitable for introducing the siRNA expression system and growth medium
7 Means for automatic acid supply for adjusting the pH of the mixture
8 Means for automatic base supply for adjusting the pH of the mixture
9 Antifoam supply
10 Outlet for exhaust gases with filter
11 Pressure indicating unit such as a pressure gauge
12 Overpressure valve
13 Filter
14 Sampling port
15 Dissolved oxygen sensor
16 pH sensor with integrated temperature sensor
17 Control panel
18 Filter
19 Bioreactor vessel
20 Growth medium
21 siRNA expression system

The invention claimed is:

1. A method of preparing a library of small interfering RNA (siRNA) expression systems for producing siRNA for silencing of target genes by inducing degradation of target gene RNA expression products, the siRNA expression system is a bacterial cell with a cloned vector, said method comprising: (i) isolating RNA of one or more target genes from a cell population; (ii) generating RNA fragments having a length of about 100 nucleotides to about 700 nucleotides from the isolated RNA; (iii) converting the RNA fragments into dsDNA fragments; (iv) cloning the dsDNA fragments into vectors for forming cloned vectors, each vector comprising one or more promoters and at least one restriction enzyme site capable of accepting the insertion of at least one dsDNA fragment such that siRNA can be produced; wherein the vector is a plasmid further comprising a siRNA-binding polypeptide expression cassette including a promoter, a sequence encoding a siRNA-binding polypeptide and a sequence encoding a siRNA-generating enzyme, wherein the siRNA-binding polypeptide is a p19 polypeptide and the siRNA-generating enzyme is an *Escherichia coli* RNase III.

2. The method of claim 1, wherein the RNA is the transcriptome of the cell population and wherein the cell population is from a human and comprises cancer cells.

3. The method of claim 1, wherein the one or more promoters are T7 promoters.

4. The method of claim 1, wherein the siRNA produced has a length of between about 19 base pairs to about 22 base

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Synthesized

<400> SEQUENCE: 1
cgtcagagga agtaacgagc tcaat                                       25

<210> SEQ ID NO 2
<211> LENGTH: 27
<212> TYPE: DNA
<213> ORGANISM: Artificial Sequence
<220> FEATURE:
<223> OTHER INFORMATION: Synthesized

<400> SEQUENCE: 2
ttgagctcgt tacttcctct gacgccc                                     27

<210> SEQ ID NO 3
<211> LENGTH: 21
<212> TYPE: DNA
<213> ORGANISM: Artificial Sequence
<220> FEATURE:
<223> OTHER INFORMATION: Synthesized

<400> SEQUENCE: 3
aagggcggct ttgccaagtg c                                           21
``` pairs and wherein the library of siRNA expression systems comprises populations of expression systems each able to express siRNA having at least about 80% complementarity over its entire length to RNA expression products of different target genes.

5. The method of claim 1, wherein step (iv) comprises:
  a) ligation of the DNA fragments with an adaptor comprising at least one restriction enzyme site matching the at least one restriction enzyme site in the vector;
  b) amplifying the dsDNA fragments with a primer matching the adaptor;
  c) digesting the dsDNA fragments by a restriction enzyme able to recognize the restriction enzyme site on the adaptor;
  d) ligating the digested dsDNA into the vector.

6. The method of claim 5, wherein the restriction enzyme site of the adaptor is a SacI restriction enzyme site and the adaptor comprises SEQ ID NO:1, and SEQ ID NO:2 as complementary strand and step a) includes adding the adaptor and a ligase.

7. The method of claim 1 further comprising a step (v) of transforming the cloned vectors into bacterial cells.

8. The method of claim 7, wherein the bacterial cells are selected from *Escherichia coli* cells and wherein the vector comprises a siRNA-binding polypeptide expression cassette including a promoter, a sequence encoding a siRNA-binding polypeptide and a sequence encoding a siRNA-generating enzyme, wherein the siRNA-binding polypeptide is a His-tagged p19 polypeptide and the siRNA-generating enzyme is an *Escherichia coli* RNase III and wherein each cloned vector comprises one or more dsDNA fragments and is transformed into a single bacterial cell.

\* \* \* \* \*